(12) United States Patent
Picha et al.

(10) Patent No.: US 9,333,081 B2
(45) Date of Patent: May 10, 2016

(54) HARD-TISSUE IMPLANT

(71) Applicant: George J. Picha, Brecksville, OH (US)

(72) Inventors: George J. Picha, Brecksville, OH (US); Dawn Thompson, Broadview Heights, OH (US)

(73) Assignee: George J. Picha, Brecksville, OH (US)

( * ) Notice: Subject to any disclaimer, the term of this patent is extended or adjusted under 35 U.S.C. 154(b) by 118 days.

(21) Appl. No.: 14/288,796

(22) Filed: May 28, 2014

(65) Prior Publication Data
US 2014/0277559 A1 Sep. 18, 2014

Related U.S. Application Data

(62) Division of application No. 13/317,719, filed on Oct. 26, 2011, now Pat. No. 8,771,354.

(51) Int. Cl.
A61F 2/28 (2006.01)
A61L 27/04 (2006.01)
(Continued)

(52) U.S. Cl.
CPC ................. *A61F 2/28* (2013.01); *A61C 8/0018* (2013.01); *A61F 2/0077* (2013.01); *A61F 2/30771* (2013.01); *A61L 27/04* (2013.01); *A61L 27/06* (2013.01); *A61L 27/18* (2013.01); *A61L 27/365* (2013.01); *A61L 27/3608* (2013.01); *A61L 27/3612* (2013.01); *A61L 27/50* (2013.01); *A61F 2002/0081* (2013.01); *A61F 2002/30224* (2013.01); *A61F 2002/30252* (2013.01); *A61F 2002/30261* (2013.01); *A61F 2002/30273* (2013.01); *A61F 2002/30838* (2013.01);
(Continued)

(58) Field of Classification Search
CPC .................. A61F 2/28; A61F 2/30771; A61F 2002/0081; A61L 27/04; A61L 27/18
See application file for complete search history.

(56) References Cited

U.S. PATENT DOCUMENTS 3,605,123 A 9/1971 Hahn
3,808,606 A 5/1974 Tronzo
(Continued)

FOREIGN PATENT DOCUMENTS

DE 33 22 803 A1 1/1985
EP 0 162 604 A1 11/1985
(Continued)

OTHER PUBLICATIONS

Bobyn, et al.; "Characteristics of bone ingrowth and interface mechanics of a new porous tantalum biomaterial"; The Journal of Bone & Joint Surgery (Br); vol. 81-B, No. 5; Sep. 1999; pp. 907-914.
(Continued)

Primary Examiner — Jason-Dennis Stewart
(74) Attorney, Agent, or Firm — Pearne & Gordon LLP

(57) ABSTRACT

Hard-tissue implants are provided that include a bulk implant, a face, pillars, and slots. The pillars are for implantation into a hard tissue. The slots are to be occupied by the hard tissue. The hard-tissue implant has a Young's modulus of elasticity of at least 10 GPa, has a ratio of the sum of (i) the volumes of the slots to (ii) the sum of the volumes of the pillars and the volumes of the slots of 0.40:1 to 0.90:1, does not comprise any part that is hollow, and does not comprise any non-pillar part extending to or beyond the distal ends of any of the pillars. Methods of making and using hard-tissue implants are also provided.

11 Claims, 11 Drawing Sheets
(2 of 11 Drawing Sheet(s) Filed in Color)

(51) Int. Cl.

| | | |
|---|---|---|
| *A61L 27/06* | (2006.01) | |
| *A61L 27/18* | (2006.01) | |
| *A61L 27/36* | (2006.01) | |
| *A61L 27/50* | (2006.01) | |
| *A61F 2/00* | (2006.01) | |
| *A61F 2/30* | (2006.01) | |
| *A61C 8/00* | (2006.01) | |

(52) U.S. Cl.
CPC .................. *A61F2002/30878* (2013.01); *A61F 2310/00359* (2013.01); *A61L 2400/18* (2013.01); *A61L 2430/02* (2013.01)

(56) References Cited

U.S. PATENT DOCUMENTS

| | | |
|---|---|---|
| 3,855,638 A | 12/1974 | Pilliar |
| 4,237,559 A | 12/1980 | Borom |
| 4,608,052 A | 8/1986 | Van Kampen et al. |
| 4,865,603 A | 9/1989 | Noiles |
| 5,207,709 A | 5/1993 | Picha |
| 5,236,453 A | 8/1993 | Picha |
| 5,263,953 A | 11/1993 | Bagby |
| 5,545,226 A | 8/1996 | Wingo et al. |
| 5,876,457 A | 3/1999 | Picha et al. |
| 6,071,310 A | 6/2000 | Picha et al. |
| 6,106,558 A | 8/2000 | Picha |
| 6,346,122 B1 | 2/2002 | Picha et al. |
| 6,569,201 B2 | 5/2003 | Moumene et al. |
| 7,018,418 B2 | 3/2006 | Amrich et al. |
| 7,041,140 B2 | 5/2006 | Picha |
| 7,205,051 B2 | 4/2007 | King et al. |
| 7,250,550 B2 | 7/2007 | Overby et al. |
| 7,347,873 B2 | 3/2008 | Paul et al. |
| 7,556,648 B2 | 7/2009 | Picha et al. |
| 2002/0040242 A1 | 4/2002 | Picha et al. |
| 2004/0181286 A1 | 9/2004 | Michelson |
| 2005/0049706 A1 | 3/2005 | Brodke et al. |
| 2005/0246021 A1 | 11/2005 | Ringeisen et al. |
| 2006/0015184 A1 | 1/2006 | Winterbottom et al. |
| 2008/0287910 A1 | 11/2008 | Picha |
| 2009/0069904 A1 | 3/2009 | Picha |
| 2010/0256758 A1 | 10/2010 | Gordon et al. |
| 2010/0298950 A1 | 11/2010 | McDonnell et al. |
| 2011/0213467 A1 | 9/2011 | Lozier et al. |

FOREIGN PATENT DOCUMENTS

| | | |
|---|---|---|
| EP | 0 269 256 A1 | 6/1988 |
| GB | 2 181 354 A | 4/1987 |
| WO | 96/40020 A1 | 12/1996 |
| WO | 2009108789 A1 | 9/2009 |
| WO | 2013063069 A1 | 5/2013 |

OTHER PUBLICATIONS

Extended European Search Report for Corresponding Application No. EP 12843219.2; Dated Apr. 28, 2015.

Hulbert, S.F., et al.; "Materials of Construction for Artificial Bone Segments"; Research in Dental and Medical Materials (Edward Korostoff ed., 1969), pp. 19-67.

Bobyn, J.D., et al.; "The Optimum Pore Size for the Fixation of Porous-Surfaced Metal Implants by the Ingrowth of Bone"; Clinical Orthopaedics and Related Research, Section III Basic Science and Pathology, No. 150; Jul.-Aug. 1980; pp. 263-270.

Itala, A.I., et al.; "Pore Diameter of More Than 100 µm Is Not Requisite for Bone Ingrowth in Rabbits"; 58 Journal of Biomedical Materials Research (Applied Biomaterials); 2001; pp. 679-683.

Briem, D., et al.; "Response of primary fibroblasts and osteoblasts to plasma treated polyetheretherketone (PEEK) surfaces"; 16 Journal of Materials Science Materials in Medicine; 2005; pp. 671-677.

Biomechanics, BME 315; "Elastic anisotropy of bone" (http://silver.neep.wise.edu/~lakes/BME315N3.pdf—accessed Dec. 8, 2010); p. 1.

Dai, K., "Rational Utilization of the Stress Shielding Effect of Implants"; Biomechanics and Biomaterials in Orthopedics (ed. Dominique G. Poitout, Springer-Verlag London Limited, Singapore, 2004); pp. title, copyright, and 208-215.

McPherson, E.J., "Adult Reconstruction"; Review of Orthopaedics: Expert Consult; Fifth Edition (ed. Mark D. Miller, Saunders Elsevier, U.S., 2008); pp. 312-313, Section 4; "Complications in fixation," subsection a, "Stress shielding.".

HARD-TISSUE IMPLANT

RELATED APPLICATIONS

This application is a divisional of U.S. patent application Ser. No. 13/317,719, filed Oct. 26, 2011, the entire disclosure of which is hereby incorporated herein by reference.

TECHNICAL FIELD

The present disclosure relates generally to a hard-tissue implant, and more particularly to a hard-tissue implant including a bulk implant, a face, pillars, and slots.

BACKGROUND

Conventional hard-tissue implants include implants designed to promote ingrowth of hard tissue based on forming a tissue/implant interface in which the implant forms a continuous phase and the tissue forms a discontinuous phase, e.g. based on the implant having a concave and/or porous surface into which the hard tissue can grow, and designed to have add-on surface modifications, e.g. modifications added based on sintering.

For example, Van Kampen et al., U.S. Pat. No. 4,608,052, discloses an implant for use in a human body having an integral attachment surface adapted to permit ingrowth of living tissue. The implant surface is defined by a multiplicity of adjacent, generally concave surface parts having intersecting, generally aligned rims defining an inner attachment surface portion and by a multiplicity of spaced posts projecting from the inner attachment surface. Van Kampen also discloses that implants have been provided with porous surfaces, as described in U.S. Pat. Nos. 3,605,123, 3,808,606, and 3,855,638.

Also for example, J. D. Bobyn et al, 150 Clinical Orthopaedics & Related Research 263 (1980), discloses that a pore size range of approximately 50 to 400 µm provided an optimal or maximal fixation strength (17 MPa) in the shortest time period (8 weeks) with regard to cobalt-base alloy implants with powder-made porous surfaces. Specifically, implants were fabricated based on coating cylindrical rods of cast cobalt-base alloy with cobalt base alloy powder in four particle size ranges. The particle size ranges were as follows: 25 to 45 µm; 45 to 150 µm; 150 to 300 µm; and 300 to 840 µm. The corresponding pore size ranges of the particles were as follows: 20 to 50 µm; 50 to 200 µm; 200 to 400 µm; and 400 to 800 µm, respectively. The particles were then bonded to the rods based on sintering. All implants were manufactured to have a maximal diameter of 4.5 mm and a length of 9.0 mm. The implants were surgically inserted into holes in dog femurs and bone ingrowth was allowed to proceed. After varying periods of time (4, 8, or 12 weeks), the maximum force required to dislodge the implants was determined. Implants with a pore size lower than 50 µm yielded relatively low fixation strengths at all time points, while implants with a pore size higher than 400 µm exhibited relatively high scatter with regard to fixation strengths, thus indicating that a pore size range of approximately 50 to 400 µm provided an optimal or maximal fixation strength.

Conventional hard-tissue implants also include implants having surface texturing, e.g. barbs or pillars, to make it difficult to withdraw the implants from hard tissue or to more effectively mechanically anchor at an early date or affix into adjoining hard tissue.

For example, Amrich et al., U.S. Pat. No. 7,018,418, discloses implants having a textured surface with microrecesses such that the outer surface overhangs the microrecesses. In one embodiment, unidirectional barbs are produced in the surface that can be inserted into bone or tissue. The directional orientation of the barbs is intended to make it difficult to withdraw from the bone or tissue.

Also for example, Picha, U.S. Pat. No. 7,556,648, discloses a spinal implant, i.e. an implant for use in fusing and stabilizing adjoining spinal vertebrae, including a hollow, generally tubular shell having an exterior lateral surface, a leading end, and a trailing end. The exterior surface includes a plurality of pillars arranged in a non-helical array. Each pillar has a height of 100 to 4,500 µm and a lateral dimension at the widest point of 100 to 4,500 µm. The exterior surface also has a plurality of holes therethrough to permit bone ingrowth therethrough.

Unfortunately, interfaces of hard tissue and hard-tissue implants in which the hard tissue is in a discontinuous phase may be susceptible to stress shielding, resulting in resorption of affected hard tissue, e.g. bone resorption, over time. Also, addition of surface texturing to implants by sintering can result in the surface texturing occupying an excessive volume of corresponding hard tissue/implant interfaces, leaving insufficient space for hard tissue. In addition, spinal implants are designed to perform under conditions relevant to spine, i.e. compression, rotational shear, and vertical shear, with the compression being essentially constant, the rotational shear being intermittent, and the vertical shear being rare, rather than conditions relevant to other hard tissues such as long bone, maxillary bone, mandibular bone, and membranous bone, i.e. load bearing conditions, including compression and tension, varying across the hard tissue and across time, and intermittent rotational and vertical shear. Accordingly, there is a need for hard-tissue implants of general applicability that address these issues and provide improvements. The device disclosed here is such an implant.

SUMMARY

A hard-tissue implant is provided that includes a bulk implant, a face, pillars, and slots. The face is an exterior surface of the bulk implant. The pillars are for implantation into a hard tissue. The pillars are distributed on the face, across an area of at least 80 mm$^2$, and extend distally therefrom. Each pillar is integral to the bulk implant, has a distal end, has a transverse area of (200 µm×200 µm) to (10,000 µm×10,000 µm), i.e. $4.0×10^4$ µm$^2$ to $1.0×10^8$ µm$^2$, and has a height of 100 to 10,000 µm. The slots are to be occupied by the hard tissue. The slots are defined by the pillars. Each slot has a width of 100 to 10,000 µm as measured along the shortest distance between adjacent pillars. The hard-tissue implant has a Young's modulus of elasticity of at least 10 GPa, and has a ratio of (i) the sum of the volumes of the slots to (ii) the sum of the volumes of the pillars and the volumes of the slots of 0.40:1 to 0.90:1. The hard-tissue implant does not include any part that is hollow, and does not include any non-pillar part extending to or beyond the distal ends of any of the pillars.

Also provided is a method of making a hard-tissue implant that, upon implantation into a hard tissue, provides immediate load transfer and prevents stress shielding. The hard-tissue implant includes a bulk implant, a face, pillars, and slots. The face is an exterior surface of the bulk implant. The pillars are for implantation into a hard tissue. The pillars are distributed on the face, across an area of at least 80 mm$^2$, and extend distally therefrom. Each pillar is integral to the bulk implant, has a distal end, has a transverse area of (200 µm×200 µm) to (10,000 µm×10,000 µm), i.e. $4.0×10^4$ µm$^2$ to $1.0×10^8$ µm$^2$, and has a height of 100 to 10,000 µm. The slots are to be occupied by the hard tissue. The slots are defined by the pillars. Each slot has a width of 100 to 10,000 µm as measured along the shortest distance between adjacent pillars. The hard-tissue implant has a Young's modulus of elasticity of at least 10 GPa, and has a ratio of (i) the sum of the volumes of the slots to (ii) the sum of the volumes of the pillars and the volumes of the slots of 0.40:1 to 0.90:1. The hard-tissue implant does not include any part that is hollow, and does not include any non-pillar part extending to or beyond the distal ends of any of the pillars. The method includes designing the hard-tissue implant such that the ratio of (i) the product of (a) the Young's modulus of the hard-tissue implant and (b) the sum of the volumes of the pillars to (ii) the product of (a) the Young's modulus of the hard tissue and (b) the sum of the volumes of the slots will be 0.80:1 to 3.8:1. The method also includes making the hard-tissue implant.

Also provided is a method of use of a hard-tissue implant in a hard tissue of an individual in need thereof. The hard-tissue implant includes a bulk implant, a face, pillars, and slots. The face is an exterior surface of the bulk implant. The pillars are for implantation into a hard tissue. The pillars are distributed on the face, across an area of at least 80 mm$^2$, and extend distally therefrom. Each pillar is integral to the bulk implant, has a distal end, has a transverse area of (200 µm×200 µm) to (10,000 µm×10,000 µm), i.e. $4.0×10^4$ µm$^2$ to $1.0×10^8$ µm$^2$, and has a height of 100 to 10,000 µm. The slots are to be occupied by the hard tissue. The slots are defined by the pillars. Each slot has a width of 100 to 10,000 µm as measured along the shortest distance between adjacent pillars. The hard-tissue implant has a Young's modulus of elasticity of at least 10 GPa, and has a ratio of (i) the sum of the volumes of the slots to (ii) the sum of the volumes of the pillars and the volumes of the slots of 0.40:1 to 0.90:1. The hard-tissue implant does not include any part that is hollow, and does not include any non-pillar part extending to or beyond the distal ends of any of the pillars. The method includes selecting the hard-tissue implant such that the ratio of (i) the product of (a) the Young's modulus of the hard-tissue implant and (b) the sum of the volumes of the pillars to (ii) the product of (a) the Young's modulus of the hard tissue and (b) the sum of the volume of the slots is 0.80:1 to 3.8:1. The method also includes implanting the hard-tissue implant in the hard-tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects, and advantages of the present disclosure are better understood when the following detailed description is read with reference to the accompanying drawings, in which.

DETAILED DESCRIPTION

Figure 1:
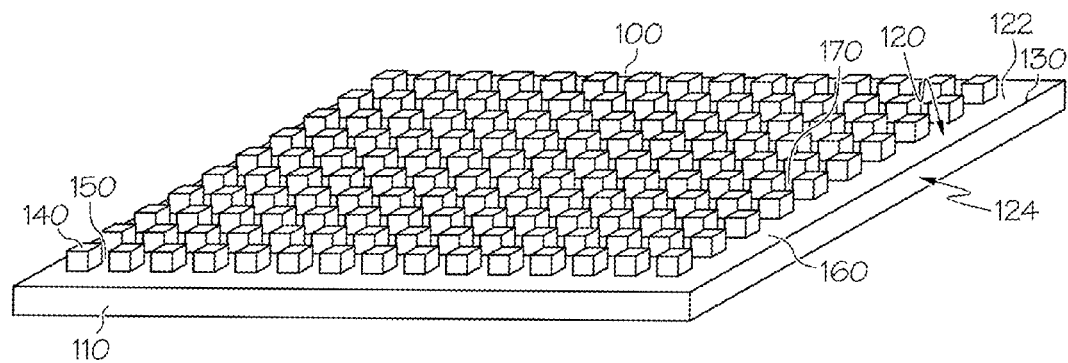
FIG. 1 is a schematic perspective view of a hard-tissue implant.

The present disclosure will now be described more fully hereinafter with reference to the accompanying drawings in which example embodiments of the invention are shown. Whenever possible, the same reference numerals are used throughout the drawings to refer to the same or like parts. However, this invention may be embodied in many different forms and should not be construed as limited to the embodiments set forth herein. These example embodiments are provided so that this disclosure will be both thorough and complete, and will fully convey the scope of the invention to those skilled in the art.

As set forth in the figures, example hard-tissue implants are provided. The hard-tissue implants provide advantages, including for example that the hard-tissue implants can promote hard-tissue remodeling and growth at the site of implantation and that the interface of the hard-tissue implants and the hard tissue can withstand substantial yield/elongation and load before failure. Without wishing to be bound by theory, it is believed that these advantages are based on properties of the hard-tissue implants and the interface resulting from implantation thereof. Specifically, the hard-tissue implants can provide immediate load transfer upon implantation and prevent stress shielding over time, thus promoting hard-tissue remodeling and growth at the site of implantation. For example, by providing immediate load transfer, the pillars of the implants may be pressed deeply into hard tissue, allowing enhanced load transfer, potentially eliminating micro-motion and migration of the implant over time, accommodating torque, and/or eliminating the need for adhesives such as cement or grout to hold the implant in place. Moreover, the interface can have a continuous phase corresponding to the hard tissue and a discontinuous phase corresponding to the hard-tissue implant. The hard tissue can also make up at least 40% of the volume of the interface, and the product of the Young's modulus of elasticity of the hard tissue and the volume of the tissue and the product of the Young's modulus of elasticity of the implant and the volume of the pillars of the implant can be well matched. Thus, the interface exhibits mechanical properties similar to those of the bulk hard tissue adjacent to the interface. The result is that the interface following implantation of a hard-tissue implant into a hard tissue is surprisingly long-lasting and resilient to load. In addition, the hard-tissue implants may promote rich vascularization of the hard tissue of the interface, enhancing wound healing, providing nutritional support, accelerating healing, remodeling, and integration of the hard tissue, and limiting the potential for infection of the hard tissue. Rapid or immediate integration of the hard tissue into the space between the pillars of the hard-tissue implant, e.g. by immediate impregnation of the implant into the surrounding tissue without need for subsequent ingrowth by the hard tissue, may also prevent detrimental cellular reactions at the interface, such as formation of fibrous tissue, seroma, or thrombosis.

As used herein, the term "hard-tissue implant" means an implant suitable for implantation in a hard tissue. Exemplary hard-tissue implants include rods, plates, screws, pins, and devices for anchoring into bone. Exemplary hard-tissue implants also include a tibial implant, a femur implant, a shoulder implant, a small joint implant, a skull plate implant, a cervical implant, and a metatarsal implant. Exemplary hard tissue implants also include a dental implant. Exemplary hard-tissue implants also include cartilage implants. Exemplary hard tissues suitable for implantation of the hard-tissue implants include bone, cartilage, calcified cartilage, non-calcified cartilage, and tissue that has become mineralized. Exemplary hard tissues also include long bone, maxillary bone, mandibular bone, and membranous bone. Exemplary hard tissues also include tibia, femur, shoulder, small joints, skull, and metatarsal. Exemplary hard tissues also include spine.

As used herein, the term "pillar" means a projection that extends distally from a face of a hard-tissue implant, that is not in direct physical contact with any other pillars or other parts of the implant other than the face, and that is for implantation into a hard tissue. Because a pillar is not in direct physical contact with any other pillars or other parts of the implant other than the face, upon implantation into a hard tissue no pillar forms a continuous phase within the resulting interface of the hard tissue and hard-tissue implant. A pillar can have a transverse area, i.e. an area of a cross-section taken relative to a vertical axis along which the pillar extends distally from the face of the implant, of, for example, (i) (200 µm×200 µm) to (10,000 µm×10,000 µm), i.e. $4.0\times10^4$ µm$^2$ to $1.0\times10^8$ µm$^2$, (ii) (200 µm×200 µm) to (2,000 µm×2,000 µm), i.e. $4.0\times10^4$ µm$^2$ to $4.0\times10^6$ µm$^2$, (iii) (250 µm×250 µm) to (1,000 µm×1,000 µm), i.e. $6.3\times10^4$ µm$^2$ to $1.0\times10^6$ µm$^2$, (iv) (300 µm×300 µm) to (500 µm×500 µm), i.e. $9\times10^4$ µm$^2$ to $2.5\times10^5$ µm$^2$, (v) (350 µm×350 µm) to (450 µm×450 µm), i.e. $1.2\times10^5$ µm$^2$ to $2.0\times10^5$ µm$^2$, or (vi) (395 µm×395 µm) to (405 µm×405 µm), i.e. $1.6\times10^5$ µm$^2$. Of note, the expression of transverse areas of pillars as squares of linear dimensions, i.e. (200 µm×200 µm), here and throughout this application, is for purposes of convenience only and is not intended to limit any pillars so described to square shapes, square transverse areas, or square cross-sections. A pillar can have a pillar height, i.e. the height of the pillar from the face of the hard-tissue implant to the distal end of the pillar, of, for example, 100 to 10,000 µm, 100 to 5,000 µm, 200 to 2,500 µm, 300 to 1,000 µm, 400 to 600 µm, 450 to 550 µm, 490 to 510 µm, or 500 µm. A pillar can have a volume, i.e. product of pillar transverse area and pillar height, of, for example (i) (200 µm×200 µm×100 µm) to (10,000 µm×10,000 µm×10,000 µm), i.e. $4.0\times10^6$ µm$^3$ to $1.0\times10^{12}$ µm$^3$, (ii) (200 µm×200 µm×100 µm) to (2,000 µm×2,000 µm×5,000 µm), i.e. $4.0\times10^6$ µm$^3$ to $2.0\times10^{10}$ µm$^3$, (iii) (250 µm×250 µm×200 µm) to (1,000 µm×1,000 µm×2,500 µm), i.e. $1.3\times10^7$ µm$^3$ to $2.5\times10^9$ µm$^3$, (iv) (300 µm×300 µm×300 µm) to (500 µm×500 µm×1,000 µm), i.e. $2.7\times10^7$ µm$^3$ to $2.5\times10^8$ µm$^3$, (v) (350 µm×350 µm×400 µm) to (450 µm×450 µm×600 µm), i.e. $4.9\times10^7$ µm$^3$ to $1.2\times10^8$ µm$^3$, or (vi) (395 µm×395 µm×490 µm) to (405 µm×405 µm×510 µm), i.e. $7.7\times10^7$ µm$^3$ to $8.4\times10^7$ µm$^3$. A pillar can have, as seen from a top view, a square shape, a rectangular shape, a herringbone shape, a circular shape, or an oval shape, respectively, or alternatively can have other polygonal, curvilinear, or variable shapes.

As used herein, the term "slot" means the spaces between the pillars. Accordingly, the pillars define the slots. The slots can have a slot height as defined by the pillars, of, for example, 100 to 10,000 µm, 100 to 5,000 µm, 200 to 2,500 µm, 300 to 1,000 µm, 400 to 600 µm, 450 to 550 µm, or 500 µm. The slots can have a slot width as measured along the shortest distance between adjacent pillars of, for example, 100 to 10,000 µm, 100 to 7,500 µm, 100 to 3,000 µm, 150 to 1,000 µm, 175 to 450 µm, 190 to 410 µm, 190 to 210 µm, or 390 to 410 µm. The slots have a volume corresponding to the volume of the space between the pillars.

As used herein, the term "pore" refers to a void space of less than 1,000 µm in size, i.e. having a diameter of less than 1,000 µm, on or below a surface, e.g. the surface of a hard-tissue implant. Pores can occur in a material naturally, e.g. based on a natural porosity of the material, or can be introduced, e.g. by chemical or physical treatment. Pores can be continuous with respect to each other, based on being interconnected with each other below a surface, or pores can be discontinuous, based on not being interconnected with each other below a surface. Pores can be sufficiently large to allow for migration and proliferation of osteoblasts and mesenchymal cells. Accordingly, for example, a porous surface is a surface that includes void spaces of less than 1,000 µm in size in the surface, whereas a non-porous surface is a surface that does not include such a void space.

As used herein the term "hollow," when used in reference to a part of a hard-tissue implant, means that the part includes, below a surface thereof, at least one void space, e.g. cavity, hole, or the like, of more than 5,000 µm in size, i.e. having a diameter greater than 5,000 µm. Accordingly, a part that is not hollow does not include any such void space.

As used herein, the term "interface resulting from implantation of the hard-tissue implant into a hard tissue," or more simply "interface," means the product of implantation wherein the pillars of the hard-tissue implant are implanted in a hard tissue and the slots of the hard-tissue implant are occupied, partially or completely, by the hard tissue. The interface includes the pillars, the hard tissue that occupies the slots of the hard-tissue implant, any remaining unoccupied space in the slots, any hard tissue that occupies any additional space between the face of the implant and a plane defined by the distal ends of the pillars, and any hard tissue that occupies any pores on the face or the pillars. Accordingly, the interface boundaries are the face of the hard tissue implant, the internal surfaces of any pores on the face, and the bulk tissue surrounding interface. In one example embodiment, e.g. immediately after pressing the hard-tissue implant into the hard tissue and/or after remodeling and growth of the hard tissue to fill in all space between the hard-tissue implant and the hard tissue, the pillars are implanted in the hard tissue, and the slots are completely occupied by the hard tissue. In another example embodiment, e.g. after implanting the hard-tissue implant partially into the hard tissue and/or before remodeling and growth of the hard tissue to fill in all space between the hard-tissue implant and the hard tissue, the pillars are partially implanted in the hard tissue, and the slots are partially occupied by the hard tissue.

As used herein, the term "continuous," when used for example in reference to the hard-tissue of an interface, means that the hard tissue forms a single continuous phase, extending throughout and across the interface to each boundary of the interface. As used herein, the term "discontinuous," when used for example in reference to the hard-tissue implant of an interface, means that the hard-tissue implant does not form such a single continuous phase.

Hard-Tissue Implant

Considering the features of an example hard-tissue implant in more detail, FIG. 1 provides a schematic illustration in perspective view of one example hard-tissue implant 100 in perspective view for illustration purposes. As described in more detail below, the hard-tissue implant 100 can be made from a material having a Young's modulus of elasticity, i.e. a tensile modulus of elasticity, of at least 10 GPa, as measured at 21° C., including for example (i) implantable-grade polyetheretherketone, e.g. carbon-fiber-reinforced implantable-grade polyetheretherketone, which has a Young's modulus of elasticity of at least 18 GPa, (ii) titanium, which has a Young's modulus of elasticity of approximately 110 GPa, (iii) stainless steel, which has a Young's modulus of elasticity of approximately 200 GPa, (iv) cobalt-chromium alloy, which has a Young's modulus of elasticity of greater than 200 GPa, or (iv) titanium alloy, which has a Young's modulus of elasticity of approximately 105-120 GPa, all as measured at 21° C. The hard-tissue implant 100 can be also made from a hard tissue obtained from a human or animal, e.g. an autologous hard tissue, an allogeneic hard tissue, a xenogeneic hard tissue, human cartilage, animal cartilage, a human bone, an animal bone, or a cadaver bone. Such hard tissues obtained from a human or animal can have a Young's modulus of elasticity of, e.g. 10 to 18 GPa. Such hard tissues obtained from a human or animal can also be treated, in advance of implantation, to decrease or eliminate the capacity of the hard tissue to elicit an immune response in an individual upon implantation into the individual. The hard-tissue implant can also be made from more than one of the above-noted materials and/or hard tissues. Accordingly, the hard-tissue implant 100 has a Young's modulus of elasticity of at least 10 GPa, for example 18 to 230 GPa, 18 to 25 GPa, 100 to 110 GPa, 190 to 210 GPa, 200 to 230 GPa, 105 to 120 GPa, or 10 to 18 GPa.

As shown in FIG. 1, the hard-tissue implant 100 includes a bulk implant 110, a face 120, pillars 140, and slots 150.

Considering the bulk implant 110 in more detail, as shown in FIG. 1 the bulk implant 110 forms the core of the hard-tissue implant 100 and can have a three-dimensional rectangular prism shape, although cuboidal, cylindrical, pyramidal, conical, and other three-dimensional shapes may be used in further examples. The bulk implant 110 can be made from one or more of the materials or hard tissues noted above with respect to the implant 100, e.g. a material such as implantable-grade polyetheretherketone, titanium, stainless steel, cobalt-chromium alloy, or titanium alloy, or e.g. a hard tissue obtained from a human or animal such as an autologous hard tissue, an allogeneic hard tissue, a xenogeneic hard tissue, human cartilage, animal cartilage, a human bone, an animal bone, or a cadaver bone.

The bulk implant 110 can be porous or non-porous. For example, the bulk implant 110 can include one or more surfaces that are porous, and/or can be made from one or more materials that are porous. Such porous surfaces can include pores having diameters of, e.g. 1 to 900 µm, 100 to 800 µm, or 200 to 600 µm. Also for example, the bulk implant 110 can include only surfaces that are non-porous, and/or can be made only from one or more materials that are non-porous.

Figure 2:
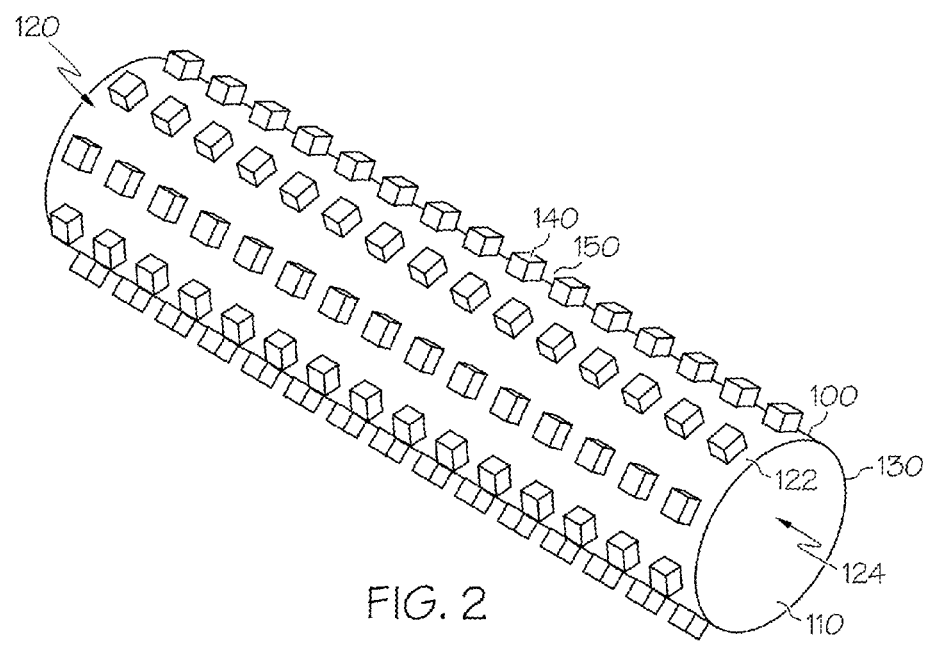
FIG. 2 is another schematic perspective view of a hard-tissue implant.
Figure 3:
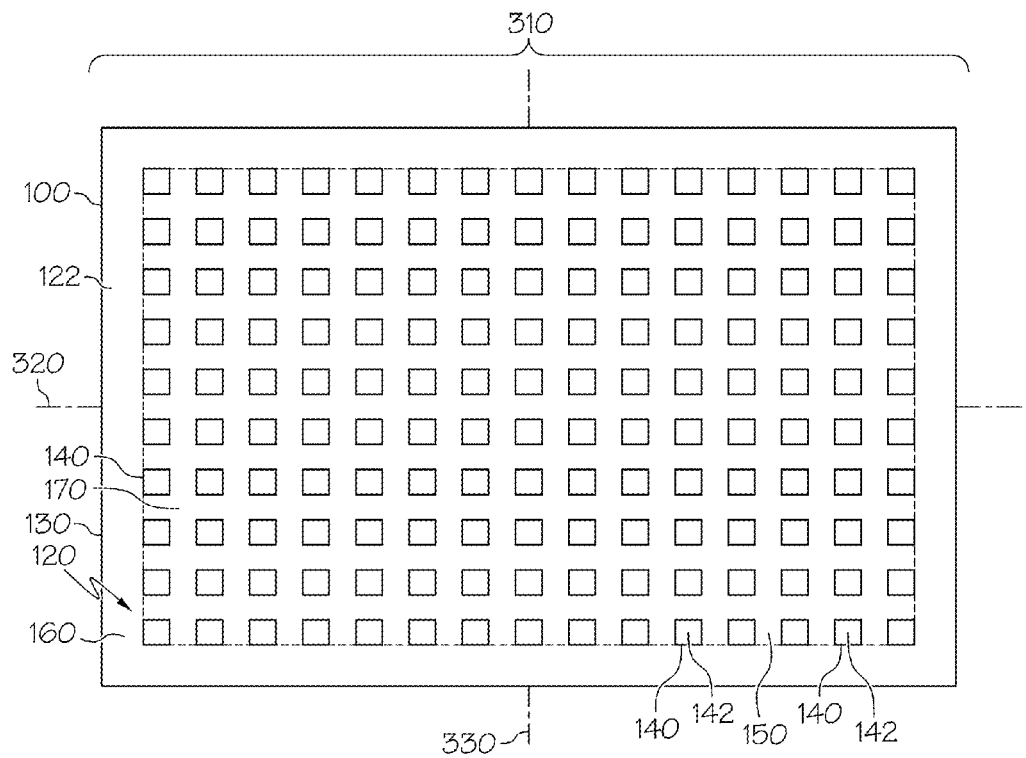
FIG. 3 is a schematic top plan view of a hard-tissue implant.

Considering now the face 120 in more detail, as shown in FIG. 1 the face 120 of the hard-tissue implant 100 is an exterior surface of the bulk implant 110, having a total area 160. As shown in FIG. 1, the face 120 can be flat, i.e. have a flat contour. Alternatively, as shown in FIG. 2, the face 120 can be cylindrical, i.e. have a cylindrical contour. As further alternatives, the face 120 can have other angular, curvilinear, and/or irregular contours. As shown in FIG. 3, the face 120 can have a rectangular peripheral shape as seen from a top view, although other polygonal, curvilinear, or other shapes may be used in further examples. As shown in FIGS. 1 and 2, the face can be defined by an edge 130. For example, as shown in FIG. 1, the edge 130 can be a single continuous edge that defines the face 120. Also for example, as shown in FIG. 2, the edge 130 can be two edges that are discontinuous with respect to each other that together define the face 120. Also for example, the edge 130 can be three or more edges that are discontinuous with respect to each other that together define the face 120. As shown in FIGS. 1 and 2, the edge 130 and the pillars 140 closest to the edge 130 can define a peripheral border 122 of the face 120. As also shown in FIGS. 1 and 2, the edge 130 can define an intersection between the face 120 and one or more adjacent faces 124 of the hard-tissue implant 100. As shown, the face 120 and the one or more adjacent faces 124 may intersect at the edge 130 at a right angle, although the face 120 and the one or more adjacent faces 124 may also intersect at other angles, e.g. acute angles, obtuse angles, or varying angles. As also shown, the edge 130 can be sharp, although other rounded, angular, smooth, and/or irregular edges may be used in further examples. The face 120 can be porous, e.g. including pores having diameters of, e.g. 1 to 900 µm, 100 to 800 µm, or 200 to 600 µm, or the face 120 can be non-porous. The bulk implant 110 can include more than one face 120, e.g. two, three, four, five, or more faces 120.

Considering now the pillars 140 in more detail, the pillars 140 are for implantation into a hard tissue. The hard tissue can be selected, for example, from the group consisting of bone, cartilage, calcified cartilage, non-calcified cartilage, and tissue that has become mineralized. The hard tissue can also be selected, for example, from the group consisting of long bone, maxillary bone, mandibular bone, and membranous bone. The hard tissue can also be selected, for example, from the group consisting of tibia, femur, shoulder, small joints, skull, and metatarsal. The hard tissue can also be, for example, spine.

As shown in FIG. 3, the pillars 140 are distributed on the face 120 of the hard-tissue implant 100, across an area 170 of the face 120 of at least 80 mm². For example, the pillars 140 can be distributed in a regular pattern 310 on the face 120 of the hard-tissue implant 100, across the area 170 of the face 120. In this regard, the pillars 140 can be distributed in even rows along a horizontal axis 320 and a vertical axis 330 of the face 120, and can be distributed along a given row uniformly with respect to the distances between the centers 142 of the pillars 140 in the row. Also for example, the pillars 140 can also be distributed in other regular patterns, e.g. the pillars 140 can be distributed in rows that are even with respect to the horizontal axis 320 but not the vertical axis 330, or vice versa, the pillars 140 in one row may be offset from the pillars 140 in adjacent rows, the pillars 140 may be arranged in a spiral pattern, etc. Also for example, the pillars 140 can be distributed on the face 120 of the hard-tissue implant 100 in irregular patterns or randomly. For example, the pillars 140 can be distributed on the face 120 of the hard-tissue implant 100 such that the pillars 140 are packed more densely on one area of the face 120 and less densely on another area of the face 120. Moreover, for a bulk implant 110 including more than one face 120 across which pillars 140 are distributed, the pillars 140 can be distributed differently on the various faces 120, e.g. in different regular patterns 310, in different irregular patterns, and/or packed at different densities.

As shown in FIGS. 1 and 3, the pillars 140 can be distributed on the face 120 of the hard-tissue implant 100 such that none of the pillars 140 are located at an edge 130, i.e. the face 120 can have a peripheral border 122 that is not occupied by any pillars 140, resulting in the area 170 of the face 120 across which the pillars 140 are distributed being less than the total area 160 of the face 120. In other example embodiments the pillars 140 can be distributed on the face 120 of the hard-tissue implant 100 such that at least some of the pillars 140 are located at an edge 130, e.g. the area 170 of the face 120 across which the pillars 140 are distributed can be equal to the total area 160 of the face 120.

Figure 4:
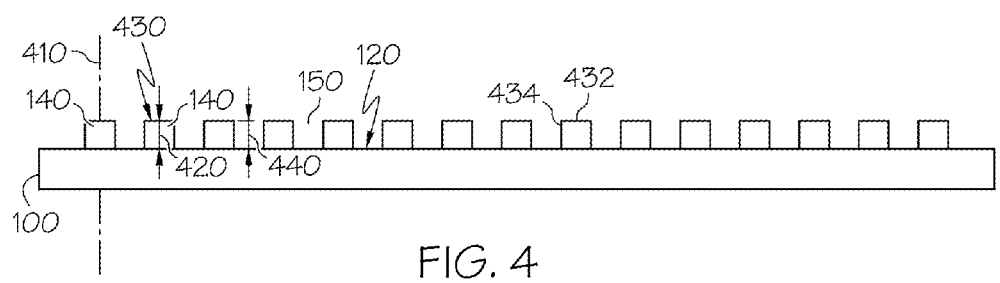
FIG. 4 is a schematic side elevational view of a hard-tissue implant.

As shown in FIG. 4, the pillars 140 extend distally from the face 120 of the hard-tissue implant 100. For example, the pillars 140 can extend distally along a vertical axis 410 from the face 120 of the hard-tissue implant 100. As shown, the pillars 140 can extend in a uniform direction, i.e. all pillars 140 extend distally at the same angle with respect to the face 120 and in the same direction. Also for example, some pillars 140 may extend distally at a different angle and/or in a different direction relative to other pillars 140, for example for a hard-tissue implant 100 for which the face 120 is not flat. As also shown, the pillars 140 can be perpendicular to the face 120, e.g. extending perpendicularly from the face 120. Also for example, the pillars 140 can extend from the face 120 at other angles and/or varying angles.

As shown in FIG. 1, each pillar 140 is integral to the bulk implant 110, i.e. the pillars 140 and the bulk implant 110 are made from the same starting material, rather than, for example, the pillars 140 being an add-on to the bulk implant 110. Like the bulk implant 110, the pillars 140 can be porous, e.g. including pores having diameters of, e.g. 1 to 900 μm, 100 to 800 μm, or 200 to 600 μm, or the pillars 140 can be non-porous.

As shown in FIG. 4, each pillar 140 has a distal end 430, corresponding to the distal-most portion of the pillar 140 relative to the face 120 of the hard-tissue implant 100. As also shown, each pillar 140 can have distal edges 432, corresponding to edges defining the distal end 430 of each pillar 140. Each pillar 140 can also have lateral edges 434, corresponding to edges of the lateral sides of each pillar 140. As further shown, the distal edges 432 and/or the lateral edges 434 can be sharp, although other rounded, angular, smooth, and/or irregular edges may be used in further examples.

Figure 5A:
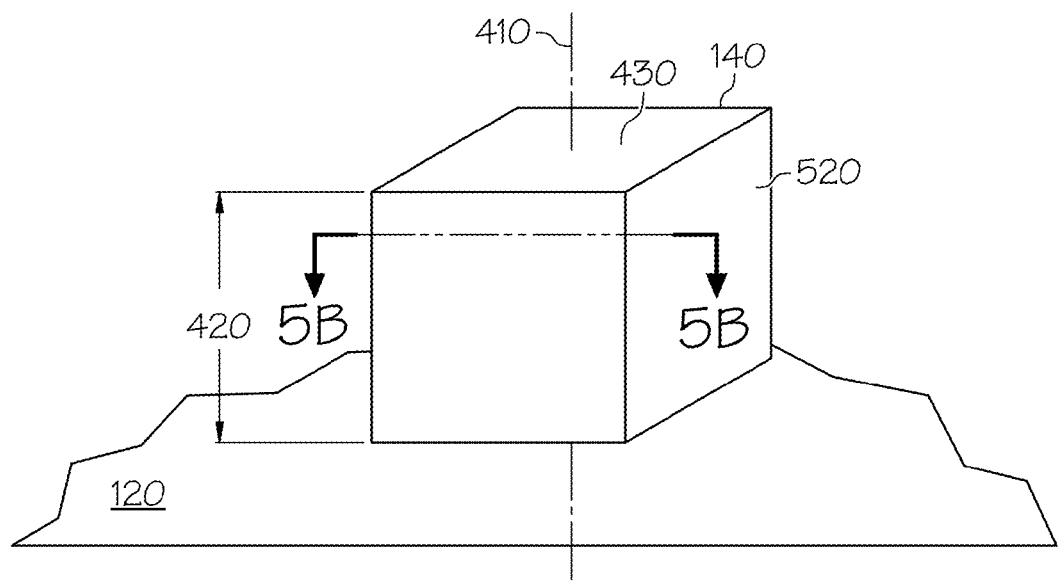
FIG. 5A is a schematic perspective view of a pillar of a hard-tissue implant.
Figure 5B:
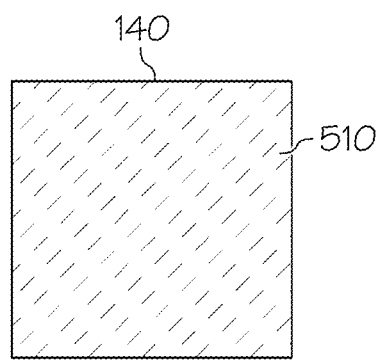
FIG. 5B is a schematic cross-sectional view of a pillar of a hard-tissue implant.
Figure 6A:
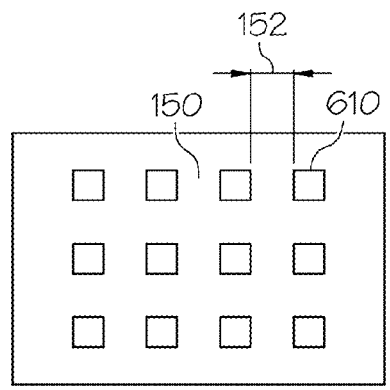
FIGS. 6A-E are schematic top plan views of a hard-tissue implant in which the circumference of the transverse area of the pillars thereof have (A) a square shape, (B) a rectangular shape, (C) a herringbone shape, (D) a circular shape, and (E) an oval shape.
Figure 6B:
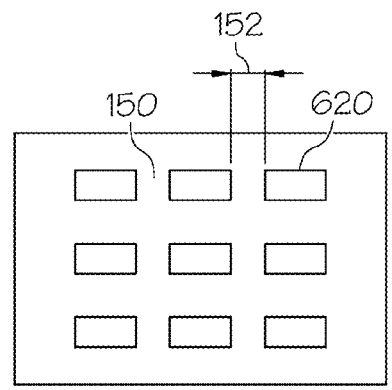
Figure 6C:
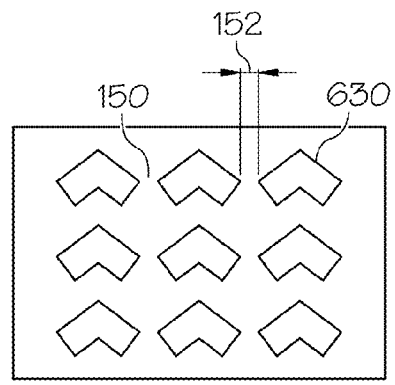
Figure 6D:
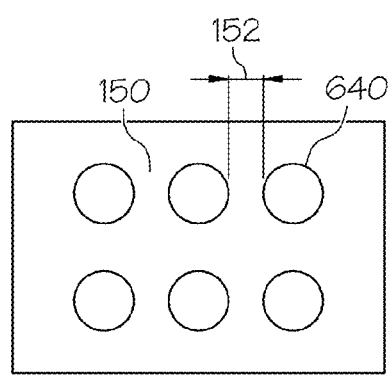
Figure 6E:
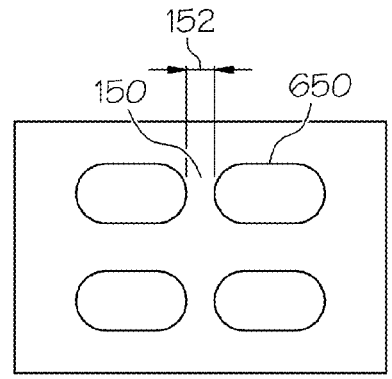

With respect to dimensions of the pillars 140, as shown in FIGS. 5A and 5B each pillar 140 has a transverse area 510, i.e. an area of a cross-section taken relative to the vertical axis 410 along which the pillar 140 extends distally from the face 120, of, for example, (i) (200 μm×200 μm) to (10,000 μm×10,000 μm), i.e. $4.0 \times 10^4$ μm$^2$ to $1.0 \times 10^8$ μm$^2$, (ii) (200 μm×200 μm) to (2,000 μm×2,000 μm), i.e. $4.0 \times 10^4$ μm$^2$ to $4.0 \times 10^6$ μm$^2$, (iii) (250 μm×250 μm) to (1,000 μm×1,000 μm), i.e. $6.3 \times 10^4$ μm$^2$ to $1.0 \times 10^6$ μm$^2$, (iv) (300 μm×300 μm) to (500 μm×500 μm), i.e. $9 \times 10^4$ μm$^2$ to $2.5 \times 10^5$ μm$^2$, (v) (350 μm×350 μm) to (450 μm×450 μm), i.e. $1.2 \times 10^5$ μm$^2$ to $2.0 \times 10^5$ μm$^2$, or (vi) (395 μm×395 μm) to (405 μm×405 μm), i.e. $1.6 \times 10^5$ μm$^2$. As shown in FIGS. 4 and 5B, each pillar 140 has a pillar height 420, i.e. the height of the pillar 140 from the face 120 of the hard-tissue implant 100 to the distal end 430 of the pillar 140, of, for example, 100 to 10,000 μm, 100 to 5,000 μm, 200 to 2,500 μm, 300 to 1,000 μm, 400 to 600 μm, 450 to 550 μm, 490 to 510 μm, or 500 μm. As shown in FIG. 5A, each pillar 140 has a volume 520, i.e. product of pillar transverse area 510 and pillar height 420, of, for example (i) (200 μm×200 μm×100 μm) to (10,000 μm×10,000 μm×10,000 μm), i.e. $4.0 \times 10^6$ μm$^3$ to $1.0 \times 10^{12}$ μm$^3$, (ii) (200 μm×200 μm×100 μm) to (2,000 μm×2,000 μm×5,000 μm), i.e. $4.0 \times 10^6$ μm$^3$ to $2.0 \times 10^{10}$ μm$^3$, (iii) (250 μm×250 μm×200 μm) to (1,000 μm×1,000 μm×2,500 μm), i.e. $1.3 \times 10^7$ μm$^3$ to $2.5 \times 10^9$ μm$^3$, (iv) (300 μm×300 μm×300 μm) to (500 μm×500 μm×1,000 μm), i.e. $2.7 \times 10^7$ μm$^3$ to $2.5 \times 10^8$ μm$^3$, (v) (350 μm×350 μm×400 μm) to (450 μm×450 μm×600 μm), i.e. $4.9 \times 10^7$ μm$^3$ to $1.2 \times 10^8$ μm$^3$, or (vi) (395 μm×395 μm×490 μm) to (405 μm×405 μm×510 μm), i.e. $7.7 \times 10^7$ μm$^3$ to $8.4 \times 10^7$ μm$^3$. As shown in FIG. 1, the pillars 140 can, for example, all have identical dimensions, e.g. identical pillar transverse areas 510, pillars heights 420, and thus identical individual volumes. Alternatively, one or more pillars 140 can have dimensions that differ from those of other pillars 140, such that the individual volumes of the one or more pillars 140 differ from those of the other pillars 140.

Turning to FIGS. 6A-6E, corresponding to a top plan view of hard-tissue implants 100 having pillars 140 of various shapes, the pillars 140 can have, as seen from a top view, a square shape 610, a rectangular shape 620, a herringbone shape 630, a circular shape 640, or an oval shape 650, respectively, or alternatively can have other polygonal, curvilinear, or variable shapes. For example, in some embodiments all pillars 140 can have the same shape, e.g. a square shape 610, a rectangular shape 620, a herringbone shape 630, a circular shape 640, or an oval shape 650, as seen from a top view. Also for example, in some embodiments not all pillars 140 have the same shape as seen from a top view.

Considering now the slots 150 in more detail, the slots 150 are to be occupied by the hard tissue. For example, upon implantation of the hard-tissue implant 100 into a hard tissue, the hard tissue can immediately occupy all or part of the space corresponding to the slots 150. This can be accomplished, for example, by pressing the hard-tissue implant 100 into the hard tissue. Moreover, to the extent that the hard tissue does not, upon implantation, immediately occupy all of the space corresponding to slots 150, the hard tissue can eventually occupy all or part of the space corresponding to the slots 150 based on remodeling and/or growth of the hard tissue over time.

Figure 7:
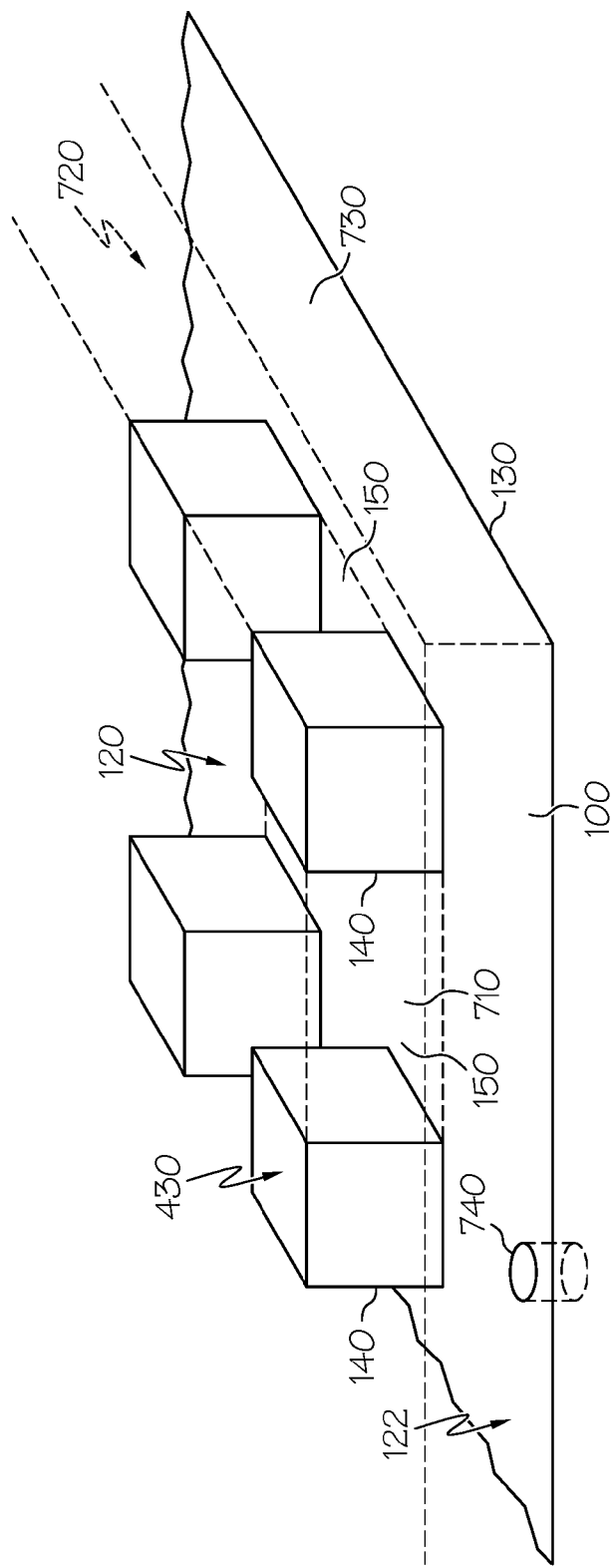
FIG. 7 is a schematic perspective view of part of a hard-tissue implant.

As shown in FIGS. 1, 3, and 4, the pillars 140 define the slots 150 therebetween, i.e. the slots 150 are the spaces between the pillars 140. Accordingly, as shown in FIG. 4, the slots 150 have a slot height 440 as defined by the pillars 140, of, for example, 100 to 10,000 μm, 100 to 5,000 μm, 200 to 2,500 μm, 300 to 1,000 μm, 400 to 600 μm, 450 to 550 μm, or 500 μm. As shown in FIGS. 6A-E, the slots 150 have a slot width 152 as measured along the shortest distance between adjacent pillars 140 of, for example, 100 to 10,000 μm, 100 to 7,500 μm, 100 to 3,000 μm, 150 to 1,000 μm, 175 to 450 μm, 190 to 410 μm, 190 to 210 μm, or 390 to 410 μm. As shown in FIG. 7, the slots 150 have a volume 710 corresponding to the volume of the space between the pillars 140.

The hard-tissue implant 100 has a ratio of (i) the sum of the volumes 710 of the slots 150 to (ii) the sum of the volumes 520 of the pillars 140 and the volumes 710 of the slots 150, of, for example, 0.40:1 to 0.90:1, 0.51:1 to 0.90:1, 0.51:1 to 0.60:1, or 0.70:1 to 0.76:1. Without wishing to be bound by theory, it is believed that this ratio determines the approximate percentages of hard tissue and hard-tissue implant 100 that will occupy the interface following implantation of the hard-tissue implant 100, e.g. that upon pressing the implant 100 into the hard tissue, or upon remodeling and growth of the hard-tissue following implantation, that the hard tissue will occupy all or essentially all of the space corresponding to the slots 150 of the hard-tissue implant 100.

More specifically, as shown in FIG. 7, the interface includes (i) the pillars 140, (ii) the slots 150 of the hard-tissue implant 100, which have a volume 710 and which, upon or following implantation, become occupied by hard tissue, (iii) any additional space between the face 120 of the implant 100 and a plane 720 defined by the distal ends 430 of the pillars 140, e.g. the space between the peripheral border 122 of the face 120 that is not occupied by pillars 140 and the plane 720, which has a volume 730 and which also becomes occupied by hard tissue, and (iv) any pores 740 on the face 120 or the pillars 140, which, depending on their size, may also become occupied by hard tissue.

Accordingly, for example, a ratio of the sum of (i) the volumes 710 of the slots 150 to (ii) the sum of the volumes 520 of the pillars 140 and the volumes 710 of the slots 150 of 0.40:1 would, following implantation of a hard-tissue implant 100 and subsequent remodeling and growth of hard tissue, wherein the implant 100 includes an edge 130 and for which pillars 140 are located at the edge 130, result in an interface that includes by volume 40% hard tissue and 60% hard-tissue implant 100, and more particularly 60% pillars 140 of the hard-tissue implant 100. Similarly, a ratio of (i) the sum of the volumes 710 of the slots 150 to (ii) the sum of the volumes 520 of the pillars 140 and the volumes 710 of the slots 150 of 0.40:1 would, following implantation of a hard-tissue implant 100 and subsequent remodeling and growth of hard tissue, wherein the implant 100 includes an edge 130 and for which no pillars 140 are located at the edge 130, result in an interface that includes by volume more than 40% hard tissue and less than 60% hard-tissue implant 100, with the percentage of hard tissue increasing, and the percentage of hard-tissue implant 100 decreasing, with increasing distance between the peripheral-most pillars 140 and slots 150 and the edge 130 of the hard-tissue implant 100. By way of further examples, ratios of 0.51:1, 0.60:1, 0.70:1, 0.76:1, and 0.90:1, would result in interfaces that include, by volume, 51% hard tissue and 49% hard-tissue implant 100, 60% hard tissue and 40% hard-tissue implant 100, 70% hard tissue and 30% hard-tissue implant 100, 76% hard tissue and 24% hard-tissue implant 100, and 90% hard tissue and 10% hard-tissue implant, respectively, for a hard-tissue implant 100 wherein the implant 100 includes an edge 130 and for which pillars 140 are located at the edge 130. Moreover, the percentage of hard tissue would increase, and the percentage of hard-tissue implant 100 would decrease, with increasing distance between the peripheral-most pillars 140 and slots 150 and the edge 130 of the hard-tissue implant 100. It is further believed that by achieving an interface that is at least 40% hard tissue, but that has a sufficient amount of the hard-tissue implant 100 to provide support and to keep the implant 100 from migrating, that the interface will exhibit properties similar to those of the bulk hard tissue adjacent to the interface, e.g. high resilience to load.

As shown in FIG. 1, the hard-tissue implant 100 does not include any part that is hollow. By this, it is meant that neither the bulk implant 110, nor any of the pillars 140, nor any other physical part (meaning additional physical components, not the slots 150) of the hard-tissue implant 100, include, below a surface thereof, any void space, e.g. cavity, hole, or the like, of more than 5,000 μm in size, i.e. having a diameter greater than 5,000 μm.

As also shown in FIG. 1, the hard-tissue implant 100 also does not include any non-pillar part extending to or beyond the distal ends 430 of any of the pillars 140. By this, it is meant that, with respect to any face 120 of the hard-tissue implant 100 from which pillars 140 extend distally, no other physical part of the hard-tissue implant 100 (meaning additional physical components, not the slots 150) extends to, or beyond, the distal ends 430 of the pillars 140. Put another way, the pillars 140 of the hard-tissue implant 100 are not recessed or sunken relative to any other part of the hard-tissue implant 100.

Without wishing to be bound by theory, it is believed that by having the hard-tissue implant 100 not include any part that is hollow and not include any non-pillar part extending to or beyond the distal ends 430 of any of the pillars 140, that the interface resulting from implantation of the hard-tissue implant 100 into the hard tissue will result in an interface that is continuous with respect to the hard tissue and discontinuous with respect to the hard-tissue implant 100. It is also believed that such an interface will further exhibit properties similar to those of the bulk hard tissue adjacent to the interface, e.g. high resilience to load.

Considering example embodiments of the hard-tissue implant 100 in more detail, in one example embodiment, the Young's modulus of the hard-tissue implant 100 is 18 to 25 GPa and the ratio of (i) the sum of the volumes 710 of the slots 150 to (ii) the sum of the volumes 520 of the pillars 140 and the volumes 710 of the slots 150 is 0.51:1 to 0.60:1. In another example embodiment, the Young's modulus of the hard-tissue implant 100 is 100 to 110 GPa and the ratio of (i) the sum of the volumes 710 of the slots 150 to (ii) the sum of the volumes 520 of the pillars 140 and the volumes 710 of the slots 150 is 0.70:1 to 0.76:1. In another example embodiment, the hard-tissue implant 100 is made of implantable-grade polyetheretherketone, the transverse area 510 of each pillar 140 is (350 μm×350 μm) to (450 μm×450 μm), the pillar height 420 of each pillar 140 is 400 to 600 μm, the slot width 152 of each slot 150 is 190 to 210 μm, and the ratio of (i) the sum of the volumes 710 of the slots 150 to (ii) the sum of the volumes 520 of the pillars 140 and the volumes 710 of the slots 150 is 0.85:1 to 1.6:1. In another example embodiment, the hard-tissue implant 100 is made of implantable-grade polyetheretherketone, the transverse area 510 of each pillar 140 is (395 μm×395 μm) to (405 μm×405 μm), the pillar height 420 of each pillar 140 is 490 to 510 μm, the slot width 152 of each slot 150 is 190 to 210 μm, and the ratio of (i) the sum of the volumes 710 of (ii) the slots 150 to the sum of the volumes 520 of the pillars 140 and volumes 710 of the slots 150 is 0.92:1 to 1.4:1. In another example embodiment, the hard-tissue implant 100 is made of titanium, the transverse area 510 of each pillar 140 is (350 μm×350 μm) to (450 μm×450 μm), the pillar height 420 of each pillar 140 is 400 to 600 μm, the slot width 152 of each slot 150 is 390 to 410 μm, and the ratio of (i) the sum of the volumes 710 of the slots 150 to (ii) the sum of the volumes 520 of the pillars 140 and the volumes 710 of the slots 150 is 2.2:1 to 3.7:1. In another example embodiment, the hard-tissue implant 100 is made of titanium, the transverse area 510 of each pillar 140 is (395 μm×395 μm) to (405 μm×405 μm), the pillar height 420 of each pillar 140 is 490 to 510 μm, the slot width 152 of each slot 150 is 390 to 410 μm, and the ratio of (i) the sum of the volumes 710 of the slots 150 to (ii) the sum of the volumes 520 of the pillars 140 and the volumes 710 of the slots 150 is 2.4:1 to 3.5:1.

Methods of Making Hard-Tissue Implants

Methods will now be described for making a hard-tissue implant that, upon implantation into a hard tissue, provides immediate load transfer and prevents stress shielding. As described above with reference to FIGS. 1-7, the hard-tissue implant 100 includes a bulk implant 110, a face 120, pillars 140, and slots 150. The face 120 is an exterior surface of the bulk implant 110. The pillars 140 are for implantation into a hard tissue. The pillars 140 are distributed on the face 120 of the hard-tissue implant 100, across an area of at least 80 mm$^2$. The pillars 140 extend distally from the face 120 of the hard-tissue implant 100. Each pillar 140 is integral to the bulk implant 110, has a distal end 430, has a transverse area 510 of (200 μm×200 μm) to (10,000 μm×10,000 μm), i.e. $4.0 \times 10^4$ µm² to 1.0×10⁸ µm², and has a pillar height 420 of 100 to 10,000 µm. The slots 150 are to be occupied by the hard tissue. The slots 150 are defined by the pillars 140. Each slot 150 has a width 152 of 100 to 10,000 µm as measured along the shortest distance between adjacent pillars 140. The hard-tissue implant 100 has a Young's modulus of elasticity of at least 10 GPa and a ratio of (i) the sum of the volumes 710 of the slots 150 to (ii) the sum of the volumes 520 of the pillars 140 and the volumes 710 of the slots 150 of 0.40:1 to 0.90:1. The hard-tissue implant 100 does not include any part that is hollow, and does not include any non-pillar part extending to or beyond the distal ends 430 of any of the pillars 140.

The method can include a step of designing the hard-tissue implant 100 such that the ratio of (i) the product of (a) the Young's modulus of the hard-tissue implant 100 and (b) the sum of the volumes 520 of the pillars 140, to (ii) the product of (a) the Young's modulus of the hard tissue and (b) the sum of the volumes 710 of the slots 150, will be, for example, 0.80:1 to 3.8:1, 0.90:1 to 3.6:1, 0.85:1 to 1.6:1, 0.92:1 to 1.4:1, 2.2:1 to 3.7:1, or 2.4:1 to 3.5:1. Without wishing to be bound by theory, it is believed that by designing the hard-tissue implant 100 in this way the interface resulting from implantation of the hard-tissue implant 100 will have a Young's modulus of elasticity similar to that of the bulk hard tissue adjacent to the interface, and again will exhibit properties similar to those of the bulk hard tissue adjacent to the interface, e.g. high resilience to load. This step can be carried out, for example by determining the features of the hard-tissue implant 100 in view of the particular hard tissue that will be the object of implantation. Features to be determined include the material from which the hard-tissue implant 100 will be made, the dimensions of the bulk implant 110 of the hard-tissue implant 100, the area 170 of the face 120 of the hard-tissue implant 100 across which pillars 140 will be distributed, and the number, distribution, size, and direction of extension of the pillars 140.

The hard tissue can be selected, for example, from the group consisting of bone, cartilage, calcified cartilage, non-calcified cartilage, and tissue that has become mineralized. The hard tissue can also be selected, for example, from the group consisting of long bone, maxillary bone, mandibular bone, and membranous bone. The hard tissue can also be selected, for example, from the group consisting of tibia, femur, shoulder, small joints, skull, and metatarsal. The hard tissue can also be, for example, spine.

The hard-tissue implant 100 can be made, for example, of a material selected from the group consisting of implantable-grade polyetheretherketone, titanium, stainless steel, cobalt-chromium alloy, and titanium alloy. The hard-tissue implant 100 can be also made, for example, from a hard tissue obtained from a human or animal selected from the group consisting of an autologous hard tissue, an allogeneic hard tissue, a xenogeneic hard tissue, human cartilage, animal cartilage, a human bone, an animal bone, and a cadaver bone.

The Young's modulus of elasticity of the hard tissue into which the hard-tissue implant 100 will be implanted can be taken into account. The Young's modulus of elasticity of the hard tissue can be determined, for example, based on previously determined values for hard tissue of that type or based on direct measurement. For example, it has been reported in the art that wet human femoral bone yields values for Young's modulus of elasticity, as determined by mechanical testing, as follows: $E_{long}$ 17 GPa, $E_{transv}$ 11.5, and $E_{transv}$ 11.5. See, e.g., Elastic anisotropy of bone, http://silver.neep.wisc.edu/~lakes/BME315N3.pdf (last accessed Dec. 8, 2010) (citing Reilly, D. T. & Burstein, A. H., The Elastic and Ultimate Properties of Compact Bone Tissue, 8 J. Biomechanics 393-405 (1975)). It has also been reported in the art that wet bovine femoral bone yields values for Young's modulus of elasticity, as determined by ultrasound, as follows: $E_{long}$ 22 GPa, $E_{transv}$ 15, and $E_{transv}$ 12. See, e.g., Elastic anisotropy of bone (citing Van Buskirk, W. C. & Ashman, R. B., The Elastic Moduli of Bone, in Mechanical Properties of Bone, Joint ASME-ASCE Applied Mechanics, Fluids Engineering and Bioengineering Conference, Boulder, Colo., 1981). It has also been reported in the art that the stiffness of compact bone tissue varies with the type of bone, e.g. the Young's moduli of fibular bone and tibial bone are about 18% greater and 7% greater, respectively, than the Young's modulus of femoral bone. See, e.g., Elastic anisotropy of bone.

Also, the hard-tissue implant 100 can include the various example embodiments as disclosed above.

Thus, for example, the hard-tissue implant 100 can be designed for implantation in, for example, a femur. The hard-tissue implant 100 can be made, for example, of implantable-grade polyetheretherketone, which has a Young's modulus of elasticity of 18 GPa. The hard-tissue implant 100 can be designed such that the bulk implant 110 thereof has a three-dimensional rectangular prism shape with a length of 12 mm, a width of 8 mm, and a height of 3 mm. The area 170 of the face 120 across which the pillars 140 are distributed can be designed, for example, to be 11.2 mm×7.6 mm, i.e. 85 mm², and to have a flat contour. The hard-tissue implant 100 can include, for example, pillars 140 distributed in a regular pattern of 19 columns across the length of the bulk implant 110 and 13 rows across the width of the bulk implant 110, for a total of 247 pillars 140. The pillars 140 can be designed to have, for example, a square shape as seen in a top view, each pillar 140 having a length of 400 µm, a width of 400 µm, and a height of 500 µm. The pillars 140 can also extend perpendicularly from the face 120.

From the foregoing, it will also be appreciated that this design would result in a sum of (i) the volumes 520 of the pillars 140 and (ii) the volumes 710 of the slots 150 being equal to the product of (i) the area 170 of the face 120 across which the pillars 140 are distributed and (ii) the pillar height 420 of the pillars 140, the product in this case being (1.12×10⁴ µm×7.6×10³ µm×500 µm), i.e. 4.26×10¹⁰ µm³.

It will also be appreciated that this design would result in each pillar 140 having a transverse area 510 of (400 µm×400 µm), i.e. 1.6×10⁵ µm². It will also be appreciated that the sum of the volumes 520 of the pillars 140 could be determined from the product of (i) the number of pillars 140 on the face 120, (ii) the transverse area 510 of each pillar 140, and (iii) the pillar height 420 of each pillar 140, the product in this case being (19×13×400 µm×400 µm×500 µm), i.e. 1.98×10¹⁰ µm³.

It will also be appreciated that this design would result in slot widths 150, as measured along the shortest distance between adjacent pillars 140, of 200 µm. It will also be appreciated that the sum of the volumes 710 of the slots 150 could also be determined from the difference between (i) the product of (a) the area 170 of the face 120 across which the pillars 140 are distributed and (b) the pillar height 420 of the pillars 140 and (ii) the sum of the volumes 520 of the pillars 140, the difference in this case being (4.26×10¹⁰ µm³−1.98×10¹⁰ µm³), i.e. 2.28×10¹⁰ µm³.

From the foregoing, it will also be appreciated that the ratio of (i) the sum of the volumes 710 of the slots 150 to (ii) the sum of the volumes 520 of the pillars 140 and the volumes 710 of the slots 150 can also be determined, the ratio in this case being (2.28×10¹⁰ µm³):(4.26×10¹⁰ µm³), i.e. 0.54:1.

As can be seen from the values above, for implantation of a hard-tissue implant 100 made of implantable-grade polyetheretherketone having a Young's modulus of elasticity of 18

GPa and having the dimensions noted above, into wet human femoral bone, which as noted above has values for Young's modulus of elasticity of $E_{long}$ 17 GPa, $E_{transv}$ 11.5, and $E_{transv}$ 11.5, the ratio of (i) the product of (a) the Young's modulus of the hard-tissue implant 100 and (b) the sum of the volumes 520 of the pillars 140, i.e. $(18 \times 1.98 \times 10^{10} \ \mu m^3)$, or $3.56 \times 10^{11} \ \mu m^3$, to (ii) the product of (a) the Young's modulus of the hard tissue and (b) the sum of the volumes 710 of the slots 150, i.e. $(17 \times 2.28 \times 10^{10} \ \mu m^3)$ to $(11.5 \times 2.28 \times 10^{10} \ \mu m^3)$, or $3.88 \times 10^{11} \ \mu m^3$ to $2.62 \times 10^{11} \ \mu m^3$, is 0.92:1 to 1.4:1.

As another example, the hard-tissue implant 100 can be designed for implantation in, again for example, a femur. The hard-tissue implant 100 can be made, for example, of titanium, which has a Young's modulus of elasticity of 107 GPa. The hard-tissue implant 100 can be designed such that the bulk implant 110 thereof has a three-dimensional rectangular prism shape with a length of 12 mm, a width of 8 mm, and a height of 3 mm. The area 170 of the face 120 across which the pillars 140 are distributed can be designed, for example, to be 11.6 mm×7.6 mm, i.e. 85 mm², and to have a flat contour. The hard-tissue implant 100 can include, for example, pillars 140 distributed in a regular pattern of 15 columns across the length of the bulk implant 110 and 10 rows across the width of the bulk implant 110, for a total of 150 pillars 140. The pillars 140 can be designed to have, for example, a square shape as seen in a top view, each pillar 140 having a length of 400 μm, a width of 400 μm, and a height of 500 μm. The pillars 140 can again extend perpendicularly from the face 120.

From the foregoing, it will also be appreciated that this design would result in a sum of (i) the volumes 520 of the pillars 140 and (ii) the volumes 710 of the slots 150 being equal to the product of (i) the area 170 of the face 120 across which the pillars 140 are distributed and (ii) the pillar height 420 of the pillars 140, the product in this case being $(1.16 \times 10^4 \ \mu m \times 7.6 \times 10^3 \ \mu m \times 500 \ \mu m)$, i.e. $4.41 \ 10^{10} \ \mu m^3$.

It will also be appreciated that this design would result in each pillar 140 having a transverse area 510 of (400 μm×400 μm), i.e. $1.6 \times 10^5 \ \mu m^2$. It will also be appreciated that the sum of the volumes 520 of the pillars could be determined from the product of (i) the number of pillars 140 in accordance with the regular pattern 310 of distribution of the pillars 140, (ii) the transverse area 510 of each pillar 140, and (iii) the pillar height 420 of each pillar 140, the product in this case being (15×10×400 μm×400 μm×500 μm), i.e. $1.20 \times 10^{10} \ \mu m^3$.

It will also be appreciated that this design would also result in slot widths 150, as measured along the shortest distance between adjacent pillars 140, of 400 μm. Accordingly, it will also be appreciated that the sum of the volumes 710 of the slots 150 could also be determined from the difference between (i) the product of (a) the area 170 of the face 120 across which the pillars 140 are distributed and (b) the pillar height 420 of the pillars 140 and (ii) the sum of the volumes 520 of the pillars 140, the difference in this case being $(4.41 \times 10^{10} \ \mu m^3 - 1.20 \times 10^{10} \ \mu m^3)$, i.e. $3.21 \times 10^{10} \ \mu m^3$.

From the foregoing, it will also be appreciated that the ratio of (i) the sum of the volumes 710 of the slots 150 to (ii) the sum of the volumes 520 of the pillars 140 and the volumes 710 of the slots 150 can also be determined, the ratio in this case being $(3.21 \times 10^{10} \ \mu m^3):(4.41 \ 10^{10} \ \mu m^3)$, i.e. 0.73:1.

As can be seen from the values above, for implantation of a hard-tissue implant 100 made of implantable-grade polyetheretherketone having a Young's modulus of elasticity of 18 GPa and having the dimensions noted above, into wet human femoral bone, which as noted above has values for Young's modulus of elasticity of $E_{long}$ 17 GPa, $E_{transv}$ 11.5, and $E_{transv}$ 11.5, the ratio of (i) the product of (a) the Young's modulus of the hard-tissue implant 100 and (b) the sum of the volumes 520 of the pillars 140, i.e. $(18 \times 1.20 \times 10^{10} \ \mu m^3)$, or $1.28 \times 10^{12} \ \mu m^3$, to (ii) the product of (a) the Young's modulus of the hard tissue and (b) the sum of the volumes 710 of the slots 150, i.e. $(17 \times 3.21 \times 10^{10} \ \mu m^3)$ to $(11.5 \times 3.21 \times 10^{10} \ \mu m^3)$, or $5.45 \times 10^{11} \ \mu m^3$ to $3.69 \times 10^{11} \ \mu m^3$, is 2.4:1 to 3.5:1.

Additional alternatives for the step of designing the hard-tissue implant 100 such that the ratio of (i) the product of (a) the Young's modulus of the hard-tissue implant 100 and (b) the sum of the volumes 520 of the pillars 140 to (ii) the product of (a) the Young's modulus of the hard tissue and (b) the sum of the volumes 710 of the slots 150 will be, for example, 0.80:1 to 3.8:1, 0.90:1 to 3.6:1, 0.85:1 to 1.6:1, 0.92:1 to 1.4:1, 2.2:1 to 3.7:1, or 2.4:1 to 3.5:1, can include, for example, use of different materials for making the hard-tissue implant 100, selecting different dimensions of the bulk implant 110 of the hard-tissue implant 100, selecting a different area 170 of the face 120 of the hard-tissue implant 100 across which pillars 140 will be distributed, and/or selecting different numbers, distributions, sizes, and directions of extension of the pillars 140. For example, for design of a hard-tissue implant 100 made from a hard tissue, the relatively low Young's modulus of elasticity of the hard tissue could be taken into account, such that the hard-tissue implant 100 could be designed to yield an interface, upon implantation into a hard tissue, for which the ratio of (i) the sum of the volumes of the slots to (ii) the sum of the volumes of the pillars and the volumes of the slots is approximately 0.50:1 and the ratio of (i) the product of (a) the Young's modulus of the hard-tissue implant 100 and (b) the sum of the volumes 520 of the pillars 140 to (ii) the product of (a) the Young's modulus of the hard tissue and (b) the sum of the volumes 710 of the slots 150 will be about 1:1. Also for example, for design of a hard-tissue implant 100 for implantation into a relatively old hard tissue, e.g. a bone of an elderly person, a relative decrease in Young's modulus of elasticity associated with increasing age of a hard tissue can be taken into account in designing the hard-tissue implant 100.

The method can also include a step of making the hard-tissue implant 100 in accordance with the design. Methods for making a hard-tissue implant 100 as disclosed herein include laser cutting, injection molding, and other standard fabrication methods that are well known in the art.

Methods of Using Hard-Tissue Implants

Methods will now be described for use of a hard-tissue implant 100 in a hard tissue of an individual in need thereof. As described above with reference to FIGS. 1-7, the hard-tissue implant 100 includes a bulk implant 110, a face 120, pillars 140, and slots 150. The face 120 is an exterior surface of the bulk implant 110. The pillars 140 are for implantation into a hard tissue. The pillars 140 are distributed on the face 120 of the hard-tissue implant 100, across an area of at least 80 mm². The pillars 140 extend distally from the face 120 of the hard-tissue implant 100. Each pillar 140 is integral to the bulk implant 110, has a distal end 430, has a transverse area of 510 of (200 μm×200 μm) to (10,000 μm×10,000 μm), i.e. $4.0 \times 10^4 \ \mu m^2$ to $1.0 \times 10^8 \ \mu m^2$, and has a pillar height 420 of 100 to 10,000 μm. The slots 150 are to be occupied by the hard tissue. The slots 150 are defined by the pillars 140. Each slot 150 has a width 152 of 100 to 10,000 μm as measured along the shortest distance between adjacent pillars 140. The hard-tissue implant 100 has a Young's modulus of elasticity of at least 10 GPa and a ratio of (i) the sum of the volumes 710 of the slots 150 to (ii) the sum of the volumes 520 of the pillars 140 and the volumes 710 of the slots 150 of 0.40:1 to 0.90:1. The hard-tissue implant 100 does not include any part that is hollow, and does not include any non-pillar part extending to or beyond the distal ends 430 of any of the pillars 140.

The method includes a step of selecting the hard-tissue implant 100 such that the ratio of (i) the product of (a) the Young's modulus of the hard-tissue implant 100 and (b) the sum of the volumes 520 of the pillars 140, to (ii) the product of (a) the Young's modulus of the hard tissue and (b) the sum of the volumes 710 of the slots 150, is, for example, 0.80:1 to 3.8:1, 0.90:1 to 3.6:1, 0.85:1 to 1.6:1, 0.92:1 to 1.4:1, 2.2:1 to 3.7:1, or 2.4:1 to 3.5:1.

The method also includes a step of implanting the hard-tissue implant 100 in the hard-tissue. The implanting can be done, for example, without rotation or twisting of the hard-tissue implant 100. The implanting can also be done, for example, without use of adhesives, e.g. cement or grout. The implanting can also be done, for example, without use of screws or plating mechanisms.

The implanting can include, for example, pressing the hard-tissue implant 100 into the hard tissue, thereby providing immediate load transfer and preventing stress shielding. The pressing can be, for example, by direct compression, mechanical compression, or tapping. Such pressing can include pressing the pillars 140 of the hard-tissue implant 100 into the hard tissue, such that the pillars 140 penetrate into the hard tissue, partially or completely. For example, the hard-tissue implant 100 can be pressed into the hard-tissue such that the pillars 140 penetrate the hard-tissue to a depth of, for example, 1 to 10,000 µm, 100 to 5,000 µm, 200 to 2,500 µm, 300 to 1,000 µm, 400 to 600 µm, 450 to 550 µm, 490 to 510 µm, or 500 µm. Also for example, the pillars 140 can be pressed into the hard-tissue such that pillars 140 penetrate the hard tissue to a depth, relative to the pillar height 420 of the pillars 140, of for example 25%, 50%, 75%, and 100% of the pillar height 420 of the pillars 140.

The implanting can also include, for example, pressing the hard-tissue implant 100 into the hard tissue, such that the pillars 140 are oriented perpendicularly to the primary axis of tension and compression of the hard tissue and penetrate the hard tissue, thereby providing immediate load transfer and preventing stress shielding. The term "primary axis of tension and compression of the hard tissue," as used herein, means the main axis of the hard tissue along which forces of tension and compression are transmitted during normal function and use of the hard tissue, e.g. the long axis of a bone such as tibia or femur. Without wishing to be bound by theory, it is believed that by having the pillars 140 oriented perpendicularly to the primary axis of tension and compression of the hard tissue, and further by having the pillars 140 penetrate the hard tissue during the implanting, that immediately following the implanting the hard-tissue implant 100 will experience immediate load transfer with respect to tension and compression of the hard tissue, and that this will prevent stress shielding of the hard tissue at the interface of the hard-tissue implant 100 and the hard tissue.

Also for example, the implanting can include pressing the hard-tissue implant 100 into the hard tissue, such that the pillars 140 are oriented at an acute angle relative to the direction of the pressing and penetrate the hard tissue, thereby providing immediate load transfer and preventing stress shielding. By the pillars 140 being oriented at an acute angle relative to the direction of the pressing it is meant that pillars 140 are angled forward to at least some extent, i.e. are at an angle of less than 90°, relative to the direction of the path by which the implant 100 is pressed into the hard tissue. By being oriented at an acute angle, it is meant that a plurality of pillars 140, e.g. at least 10%, at least 20%, at least 30%, at least 40%, at least 50%, at least 60%, at least 70%, at least 80%, at least 90%, or 100%, are oriented at an acute angle, e.g. at angles ranging from 1° to 89°, 10° to 80°, 20° to 70°, 30° to 60°, 40° to 50°, 1° to 10°, 11° to 20°, 21° to 30°, 31° to 40°, 41° to 50°, 51° to 60°, 61° to 70°, 71° to 80°, 81° to 89°, 15°, 30°, 45°, 60°, or 75°, relative to the direction of the pressing. Without wishing to be bound by theory, it is believed that by having the pillars 140 oriented at an acute angle relative to the direction of the pressing, and further by having the pillars 140 penetrate the hard tissue during the implanting, that again immediately following the implanting the hard-tissue implant 100 will experience immediate load transfer with respect to tension and compression of the hard tissue, thereby providing immediate load transfer between the hard-tissue implant 100 and the hard tissue, and that this will prevent stress shielding of the hard tissue at the interface of the hard-tissue implant 100 and the hard tissue.

Also for example, the implanting can include pressing the hard-tissue implant 100 into a cavity that has been milled in the hard tissue, such that the pillars 140 penetrate the hard tissue, thereby providing immediate load transfer and preventing stress shielding. For example, the cavity can be milled to dimensions wider than that of the bulk implant 110 but narrower than the bulk implant 110 including the pillars 140, such that the pressing of the hard-tissue implant 100 into the cavity results in the pillars 140 of the hard-tissue implant 100 contacting and penetrating the hard tissue during the pressing. Also for example, the cavity that has been milled in the hard tissue can be tapered from the surface of the hard tissue inward, i.e. wider at the surface of the hard tissue and narrower with increasing depth in the hard tissue, such that the pressing of the hard-tissue implant 100 into the cavity results in the pillars 140 of the hard-tissue implant 100 contacting and penetrating the hard tissue only after the implant 100 has been pressed to some depth in the cavity. Also for example, the hard-tissue implant 100 can be tapered, such that a tapered cavity and a tapered hard-tissue implant 100 have a complementary fit, e.g. such that pressing of the hard-tissue implant 100 into the cavity results in the pillars 140 of the hard-tissue implant 100 contacting and penetrating the hard tissue only after the implant 100 has been pressed to some depth in the cavity at each area of complementary fit between the tapered cavity and the tapered hard-tissue implant 100. Without wishing to be bound by theory, it is believed that by pressing the hard-tissue implant 100 into a cavity that has been milled in the hard tissue, such that the pillars 140 penetrate the hard tissue during the implanting, that again immediately following the implanting the hard-tissue implant 100 will experience immediate load transfer with respect to tension and compression of the hard tissue, and that this will prevent stress shielding of the hard tissue at the interface of the hard-tissue implant 100 and the hard tissue.

Standard approaches for implanting the hard-tissue implant 100, pressing the hard-tissue implant 100 into hard tissue, orienting the hard-tissue implant 100 or pillars 140 thereof, and pressing the hard-tissue implant 100 into a cavity that has been milled in the hard tissue are known in the art and can be used in the methods disclosed here.

The hard tissue can be selected, for example, from the group consisting of bone, cartilage, calcified cartilage, non-calcified cartilage, and tissue that has become mineralized. The hard tissue can also be selected, for example, from the group consisting of long bone, maxillary bone, mandibular bone, and membranous bone. The hard tissue can also be selected, for example, from the group consisting of tibia, femur, shoulder, small joints, skull, and metatarsal. The hard tissue can also be, for example, spine.

The hard-tissue implant 100 can be made, for example, of a material selected from the group consisting of implantable-grade polyetheretherketone, titanium, stainless steel, cobalt-chromium alloy, and titanium alloy. The hard-tissue implant 100 can be also made, for example, from a hard tissue obtained from a human or animal selected from the group consisting of an autologous hard tissue, an allogeneic hard tissue, a xenogeneic hard tissue, human cartilage, animal cartilage, a human bone, an animal bone, and a cadaver bone.

The method can be applied to example embodiments of the hard-tissue implant 100 as disclosed above. The ratio of (i) the sum of the volumes 710 of the slots 150 to (ii) the sum of the volumes 520 of the pillars 140 and the volumes 710 of the slots 150 can be determined essentially as described above with respect to designing the hard-tissue implant 100. The ratio of (i) the product of (a) the Young's modulus of the hard-tissue implant 100 and (b) the sum of the volumes 520 of the pillars 140, to (ii) the product of (a) the Young's modulus of the hard tissue and (b) the sum of the volumes 710 of the slots 150, can also be determined essentially as described above with respect to designing the hard-tissue implant 100.

The implanting can include, for example, pressing the hard-tissue implant 100 into the hard tissue, thereby providing immediate load transfer and preventing stress shielding. Methods for pressing a hard-tissue implant 100 in a hard tissue are also known in the art.

Further aspects of the present disclosure will be understood in conjunction with one or more of the following examples, which are provided by way of illustration.

Example 1

Hard-Tissue Implants

Four types of pillared hard-tissue implants, herein designated implant 1, implant 2, implant 3, and implant 4, and a smooth control implant were designed and made.

Specifically, implants 1 to 3 were made from implantable-grade polyetheretherketone ("PEEK"), having a Young's modulus of elasticity of approximately 18 GPa. Implant 4 was made from titanium, having a Young's modulus of elasticity of approximately 107 GPa. All of the implants 1 to 4 were made to have a generally rectangular prism shape, with a length of 12 mm, a width of 8 mm, and a depth of 4 mm. The bulk implants of the implants 1 to 4 were all made with a length of 12 mm, a width of 8 mm, and a depth of 3 mm. Accordingly, the bulk implants of the implants 1 to 4 each had two faces having a length of 12 mm and a width of 8 mm. Each of the two faces was defined by a sharp edge.

Pillars were distributed in a regular pattern on the two faces of each bulk implant of implants 1 to 4, as follows.

For implant 1 (PEEK), the pillars were distributed on each of the two faces in 23 columns across the length of the bulk implant and 15 rows across the width of the bulk implant, corresponding to 345 pillars per face. The pillars were located 300 μm from the edge. The pillars were integral to the bulk implant. The pillars each had a length of 400 μm and a width of 400 μm, and thus a square shape as seen from a top view and a transverse area of $1.6 \times 10^5$ μm$^2$. The pillars each had a height of 500 μm. In accordance with this distribution, the width of the slots was 100 μm as measured along the shortest distance between adjacent pillars, and the slot height was 500 μm.

For implant 2 (PEEK), the pillars were distributed on each of the two faces in 19 columns across the length of the bulk implant and 13 rows across the width of the bulk implant, corresponding to 247 pillars per face. The pillars were located 200 μm from the edge having a length of 12 mm, and 400 μm from the edge having a length of 8 mm. The pillars were integral to the bulk implant. The pillars each had a length of 400 μm and a width of 400 μm, and thus a square shape as seen from a top view and a transverse area of $1.6 \times 10^5$ μm$^2$. The pillars each had a height of 500 μm. In accordance with this distribution, the width of the slots was 200 μm as measured along the shortest distance between adjacent pillars, and the slot height was 500 μm.

For implants 3 (PEEK) and 4 (titanium), the pillars were distributed on each of the two faces in 15 columns across the length of the bulk implant and 10 rows across the width of the bulk implant, corresponding to 150 pillars per face. The pillars were located 200 μm from the edge. The pillars were integral to the bulk implant. The pillars each had a length of 400 μm and a width of 400 μm, and thus a square shape as seen from a top view and a transverse area of $1.6 \times 10^5$ μm$^2$. The pillars each had a height of 500 μm. In accordance with this distribution, the width of the slots was 400 μm as measured along the shortest distance between adjacent pillars, and the slot height was 500 μm.

The dimensions of the pillars and slots, with respect to one of the two faces of each of the implants 1 to 4, and various ratios thereof, calculated essentially as described above, are shown in TABLES 1-3.

TABLE 1

| Implant # | Material | Pillar length × width | Slot width | Pillar and slot height |
|---|---|---|---|---|
| Implant 1 | PEEK | 400 μm × 400 μm | 100 μm | 500 μm |
| Implant 2 | PEEK | 400 μm × 400 μm | 200 μm | 500 μm |
| Implant 3 | PEEK | 400 μm × 400 μm | 400 μm | 500 μm |
| Implant 4 | Titanium | 400 μm × 400 μm | 400 μm | 500 μm |

TABLE 2

| Implant # | Material | Number of pillars (per face of implant) | Volume of pillars (per face of implant) | Volume of slots (per face of implant) | Volume of interface, i.e. total area of implant face × pillar height (per face) |
|---|---|---|---|---|---|
| Implant 1 | PEEK | 345 | $2.76 \times 10^{10}$ μm$^3$ | $1.46 \times 10^{10}$ μm$^3$ | $4.8 \times 10^{10}$ μm$^3$ |
| Implant 2 | PEEK | 247 | $1.98 \times 10^{10}$ μm$^3$ | $2.28 \times 10^{10}$ μm$^3$ | $4.8 \times 10^{10}$ μm$^3$ |
| Implant 3 | PEEK | 150 | $1.20 \times 10^{10}$ μm$^3$ | $3.21 \times 10^{10}$ μm$^3$ | $4.8 \times 10^{10}$ μm$^3$ |
| Implant 4 | Titanium | 150 | $1.20 \times 10^{10}$ μm$^3$ | $3.21 \times 10^{10}$ μm$^3$ | $4.8 \times 10^{10}$ μm$^3$ |

TABLE 3

| Implant # | Material | Ratio of (i) sum of volumes of slots to (ii) sum of volumes of pillars and volumes of slots | Ratio of (i) volume of hard tissue to (ii) volume of interface |
|---|---|---|---|
| Implant 1 | PEEK | 0.35:1 | 0.43:1 |
| Implant 2 | PEEK | 0.54:1 | 0.59:1 |
| Implant 3 | PEEK | 0.73:1 | 0.75:1 |
| Implant 4 | Titanium | 0.73:1 | 0.75:1 |

The ratios of (i) the product of (a) the Young's modulus of the hard-tissue implant and (b) the sum of volumes of the pillars to (ii) the product of (a) the Young's modulus of the hard tissue and (b) the sum of the volumes of the slots, for each of implants 1 to 4, with respect to human femur, calculated essentially as described above, are shown in TABLE 4.

TABLE 4

| Implant # | Material (Young's modulus) | Hard-tissue (Young's modulus $E_{long}$, $E_{transv}$, $E_{transv}$) | Sum of volumes of pillars | Sum of volumes of slots | Ratio* |
|---|---|---|---|---|---|
| Implant 1 | PEEK (18 GPa) | Human femur (17, 11.5, 11.5 GPa) | $2.76 \times 10^{10}$ μm³ | $1.46 \times 10^{10}$ μm³ | 2.0:1 to 3.0:1 |
| Implant 2 | PEEK (18 GPa) | Human femur (17, 11.5, 11.5 GPa) | $1.98 \times 10^{10}$ μm³ | $2.20 \times 10^{10}$ μm³ | 0.92:1 to 1.4:1 |
| Implant 3 | PEEK (18 GPa) | Human femur (17, 11.5, 11.5 GPa) | $1.20 \times 10^{10}$ μm³ | $321 \times 10^{10}$ μm³ | 0.40:1 to 0.59:1 |
| Implant 4 | Titanium (107 GPa) | Human femur (17, 11.5, 11.5 GPa) | $1.20 \times 10^{10}$ μm³ | $321 \times 10^{10}$ μm³ | 2.4:1 to 3.5:1 |

*Ratio corresponds to ratio of (i) the product of (a) the Young's modulus of the hard-tissue implant and (b) the volume of the pillars to (ii) the product of (a) the Young's modulus of the hard tissue and (b) the sum of the volumes of the slots.

The smooth control implant was made from PEEK, had dimensions of 12 mm×8 mm×3 mm, and had no pillared surfaces.

Example 2

Mechanical and Histological Testing of Hard-Tissue Implants

The mechanical and histological properties of implants 1 to 4 and the control implant, as described in Example 1, and tissue-implant interfaces thereof, were tested in an animal model. Specifically 5 large adult male mongrels were selected. IACCUC regulated and approved surgery was carried out. One each of implants 1 to 4 and the control implant were implanted in each femur of each dog, the implantation being in the diaphysis posterior shaft of the femur, the implants being implanted in a single line along the long axis of the femur, the order the implants being determined randomly, and the implants being oriented such that the 12 min axes of the implants were parallel to the long axis of the femur, and the 8 mm axes of the implants were orthogonal to the surface of the femur, i.e. the implants were implanted such that the two pillared faces of each of implants 1 to 4 were in contact with the femur. Implantation was carried out by pressing each implant into the femur. Six weeks after implantation, the mongrels were euthanized and the implants were harvested. For each of implants 1 to 4 and the control implant, six specimens were tested mechanically and two specimens were analyzed with respect to histology.

Mechanical testing was carried out as follows. Each specimen was tested via a compression push-through method based on use of a compression head and a plunger. Preparation of harvested implants included cutting bone into separate testing sections and removing medullary tissue to decrease extra resistance. The implant surface was aligned normal to the compression head. The plunger was a 3×10 mm piece of metal. A compression rate of 1 mm/min was used. The upper limit of load for the load cell was 1000N. Load (N) versus extension (mm) and load (N) to failure were measured with respect to each specimen.

Figure 8A:
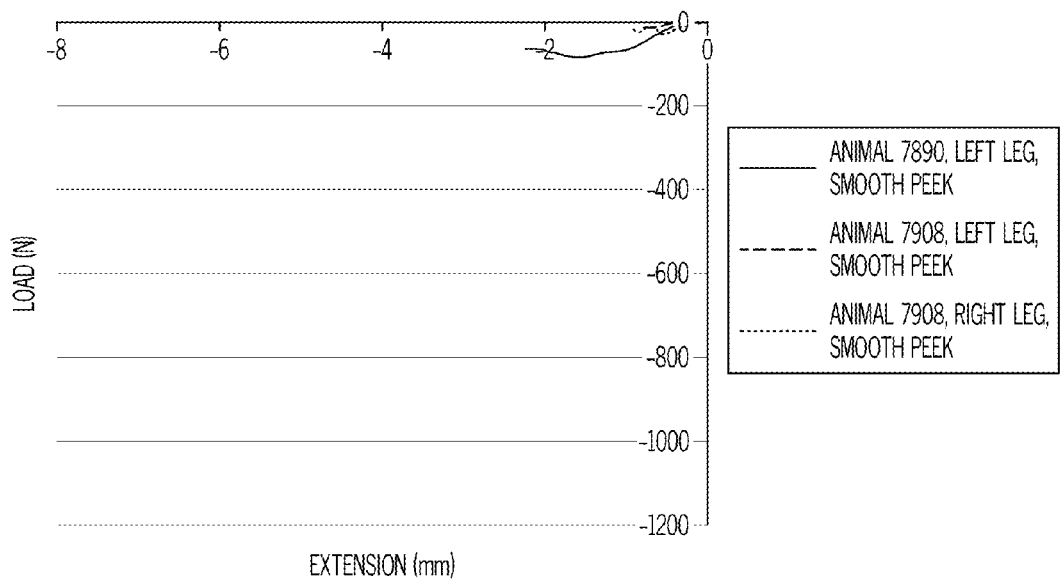
FIGS. 8A-E are graphs of canine compressive results, expressed as load (N) versus extension (mm), for canine femur implants corresponding to (A) a control implant, (B) implant 1, (C) implant 2, (D) implant 3, and (E) implant 4.
Figure 8B:
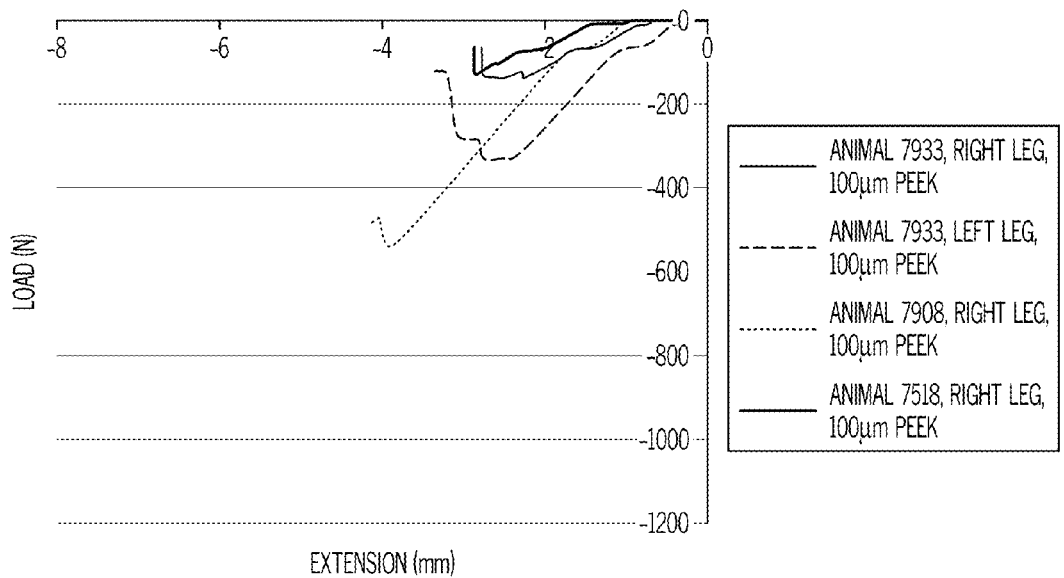
Figure 8C:
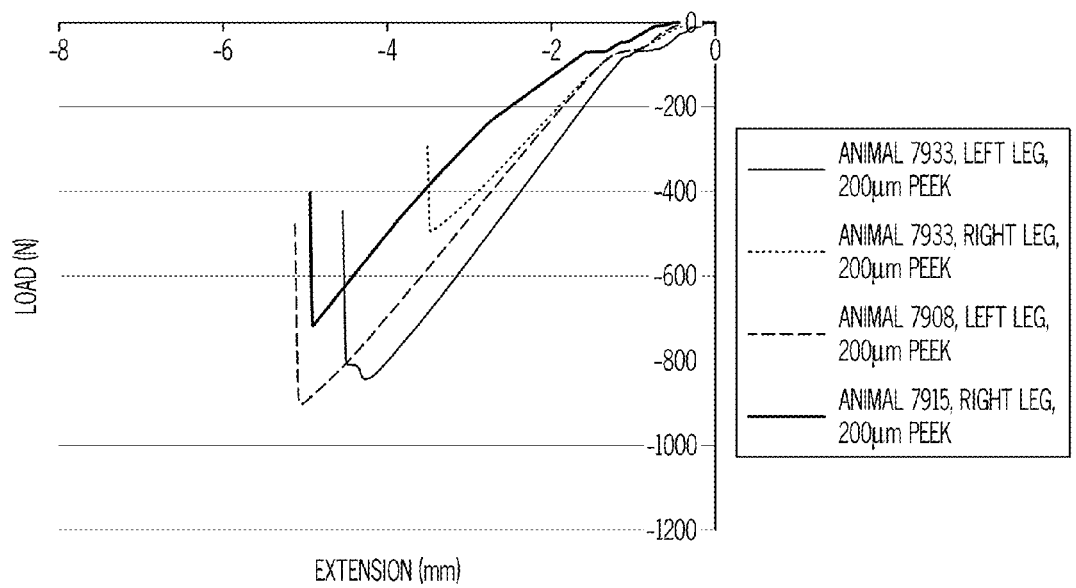
Figure 8D:
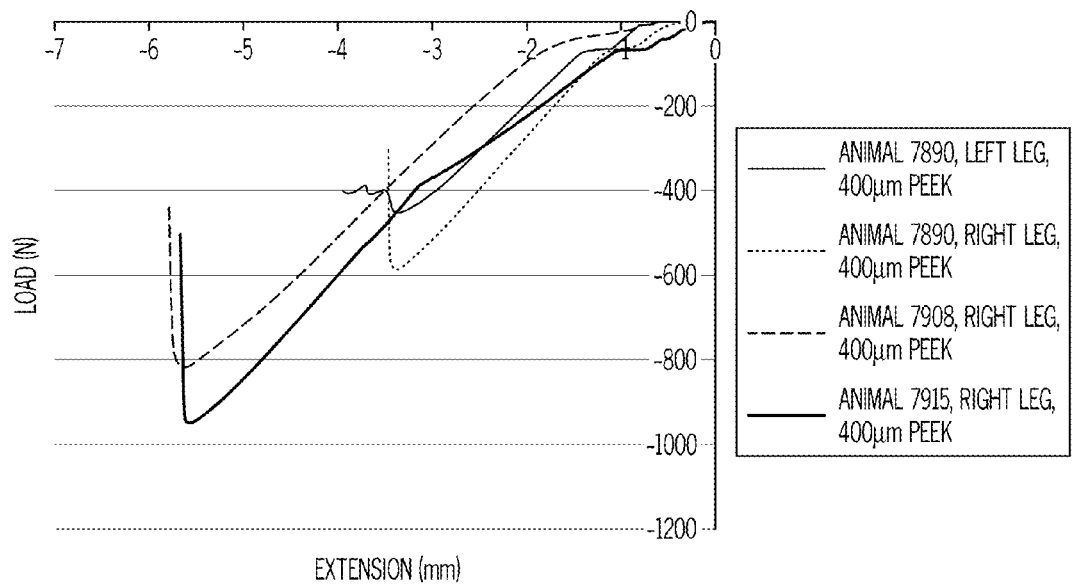
Figure 8E:
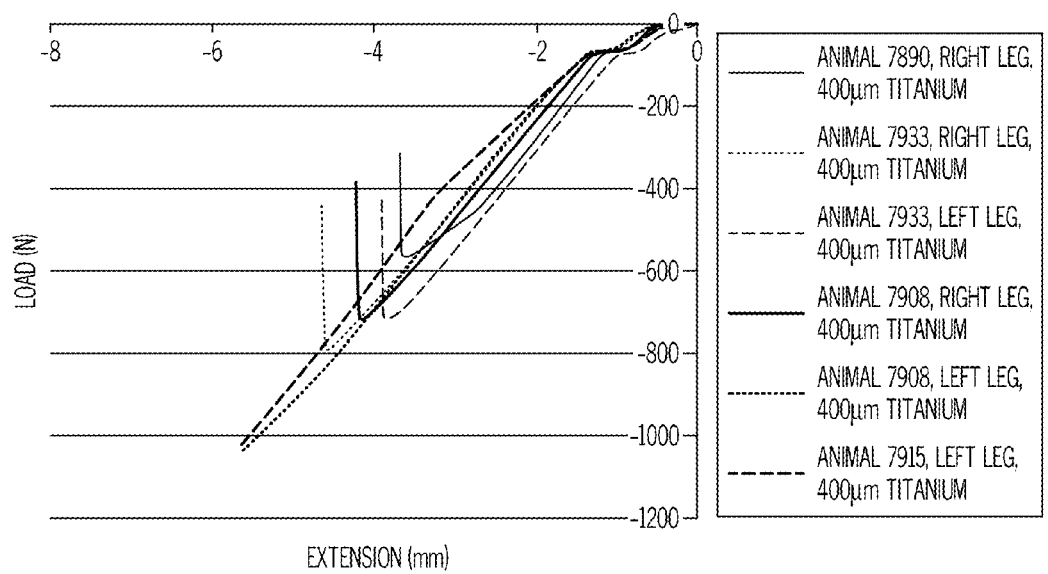

Results for extension per load are provided in FIGS. 8A-E. As can be seen in FIGS. 8C-E, the implants 2, 3, and 4, corresponding to PEEK, PEEK, and titanium implants, respectively, having slot widths of 200 μm, 400 μm, and 400 μm, respectively, underwent substantial yield/elongation before failure. Indeed two specimens of implant 4 withstood the upper limit of 1000 N load for the load cell. In contrast, as can be seen in FIGS. 8A and 8B, the control implant, which lacked pillars, and implant 1, corresponding to a PEEK implant having a slot width of 100 μm, did not undergo substantial yield/elongation before failure. The results suggest that slot widths of 200 to 400 μm enable implants to undergo substantial yield elongation before failure.

Figure 9:
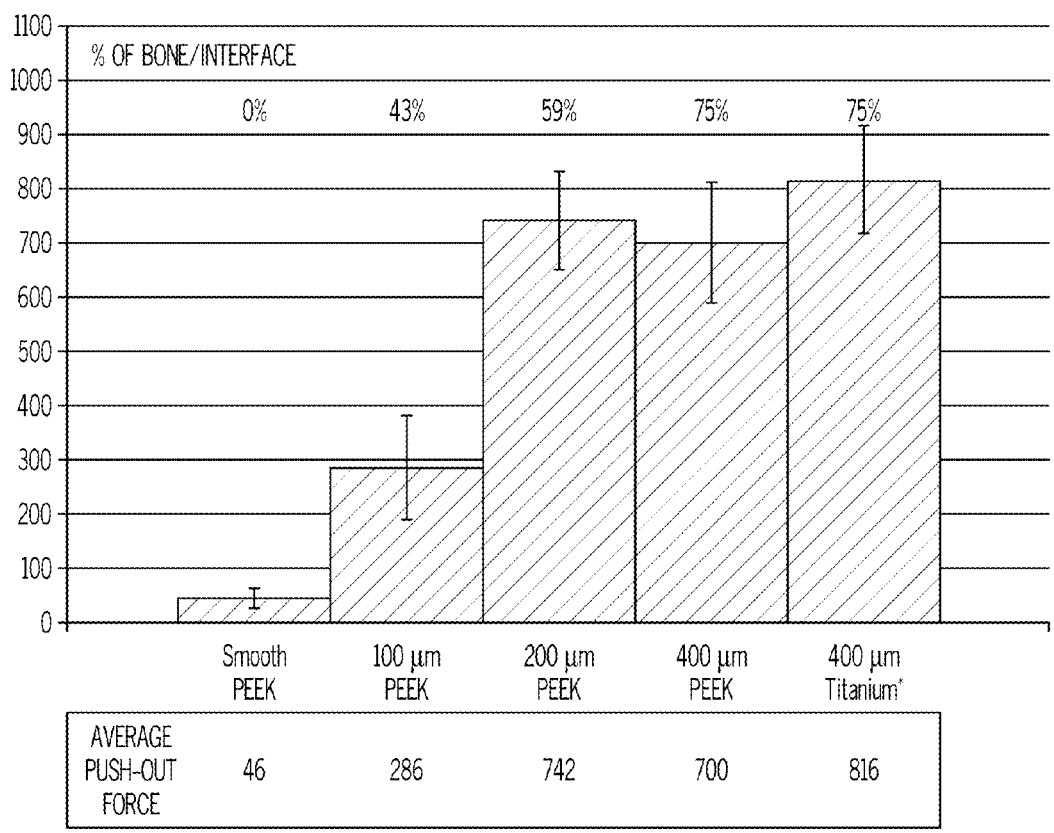
FIG. 9 is a graph of average ultimate load (N) at failure for the control implant and implants 1 to 4.
Figure 10A:
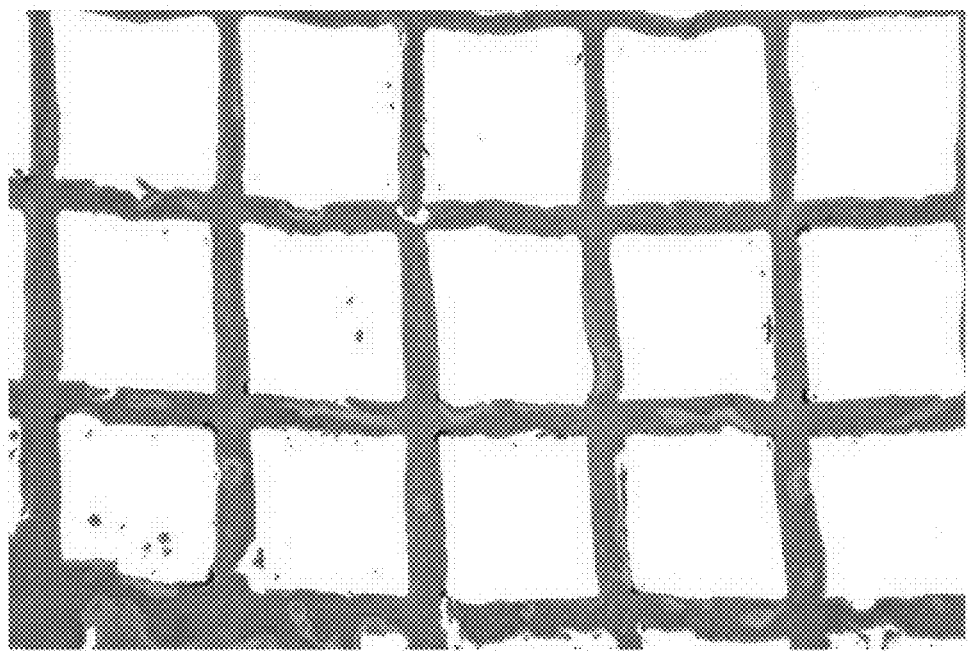
FIGS. 10A-D are histological micrographs at 4× magnification of (A) implant 1 (PEEK, 100 µm slot width) face 25 µm cut H&E stain, (B) implant 2 (PEEK, 200 µm slot width) face 25 µm trichrome stain, (C) implant 3 (PEEK, 400 µm slot width) face 25 µm trichrome stain, and (D) implant 4 (titanium, 400 µm slot width) 25 µm trichrome stain.
Figure 10B:
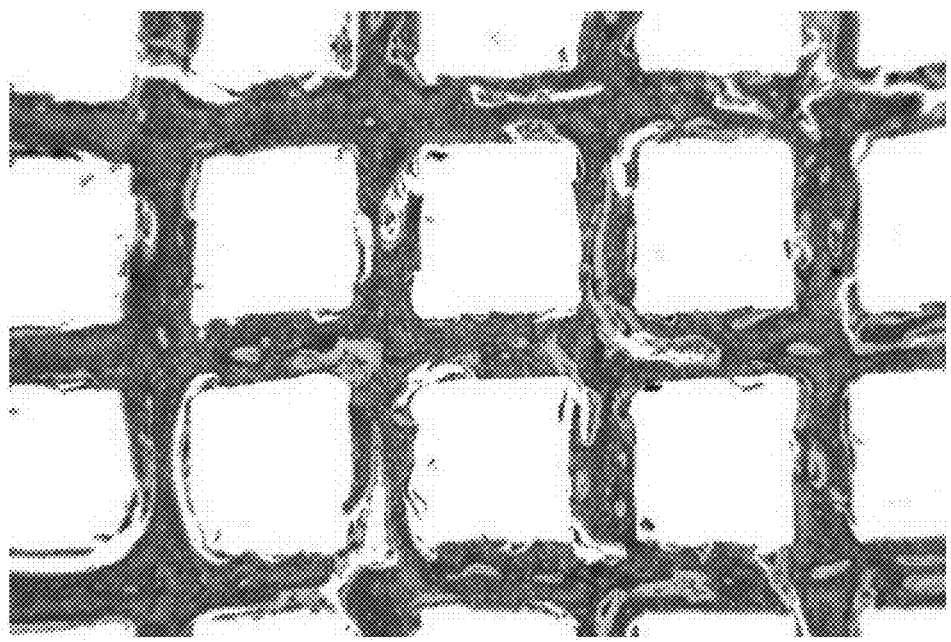
Figure 10C:
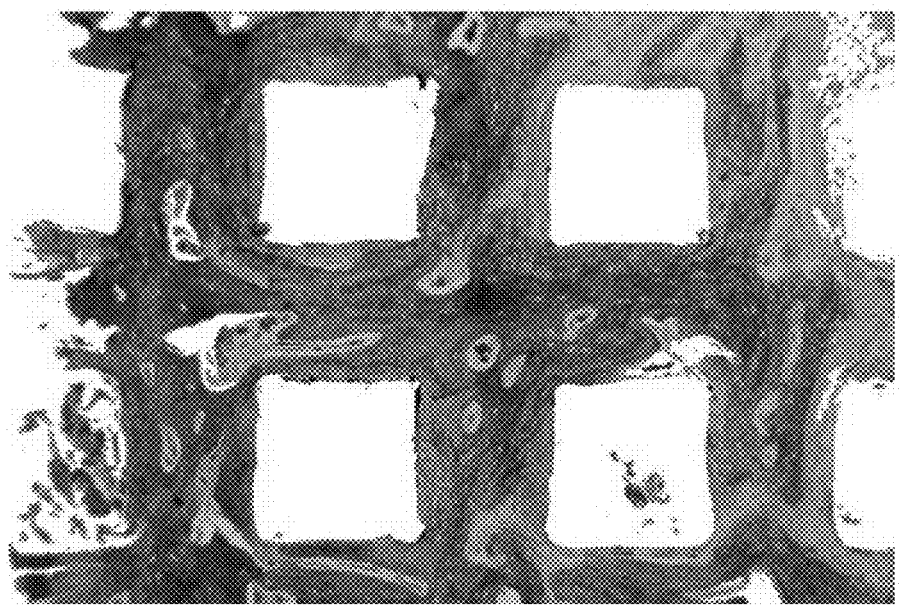
Figure 10D:
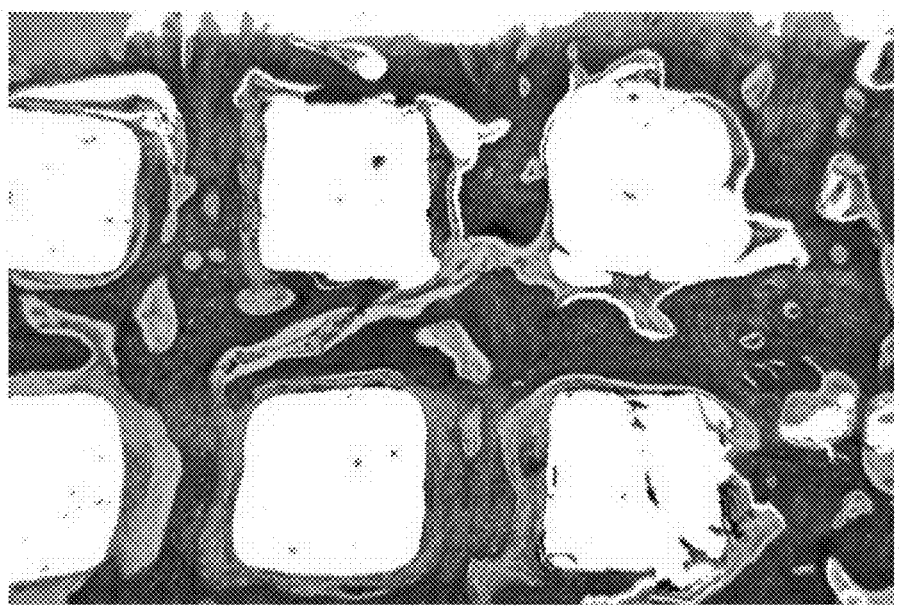

Results for load to failure are provided in FIG. 9. As can be seen, implant 4, corresponding to a titanium implant having a slot width of 400 μm, exhibited the highest average load to failure, >816 N (taking into account that two of the samples withstood the upper limit of 1000 N load for the load cell). Implant 2, corresponding to a PEEK implant having a slot width of 200 μm, exhibited the next highest load to failure, 742 N. Implant 3, corresponding to a PEEK implant having a slot width of 400 μm, exhibited the next highest load to failure, 700 N. Implant 1, corresponding to a PEEK implant having a slot width of 100 μm, and the control implant, corresponding to a PEEK implant lacking pillars, exhibited substantially lower loads to failure, 286 N and 46 N, respectively. The results suggest that slot widths of 200 to 400 μm enable implants to withstand relatively high load before failure. Moreover, considering these results in view of the data of TABLE 3, the results also suggest that hard-tissue implants having a ratio of the sum of the volumes of the slots to the sum of the volumes of the pillars and the volumes of the slots of 0.51:1 to 0.90:1, e.g. implants 2, 3, and 4, can withstand relatively high loads before failure. In addition, considering these results in view of the data of TABLE 4, the results suggest that hard-tissue implants additionally having a ratio of (i) the product of the Young's modulus of the hard-tissue implant and the sum of the volumes of the pillars to (ii) the product of the Young's modulus of the hard tissue and the sum of the volumes of the slots of between about 0.80:1 to 3.8:1, e.g. implants 2 and 4, can withstand even higher loads before failure.

Histological analyses were carried out using hematoxylin and eosin stain and trichrome stain. Exemplary results are shown in FIGS. 10A-D, corresponding to histological micrographs at 4× magnification of (A) implant 1 (PEEK, 100 μm slot width) face 25 μm cut H&E stain, (B) implant 2 (PEEK, 200 μm slot width) face 25 μm trichrome stain, (C) implant 3 (PEEK, 400 μm slot width) face 25 μm trichrome stain, and (D) implant 4 (titanium, 400 μm slot width) 25 μm trichrome stain. Results for the histological analyses indicate that implants 1 to 4, having slot widths of 100 μm, 200 μm, 400 μm, and 400 μm, respectively, all exhibited bone ingrowth in the slots thereof. The ingrowth for implant 1 was different than that of implants 2 to 4 but nonetheless occurred. Implants 2 to 4, but not implant 1, also exhibited rich vascularity in the slots thereof. No significant inflammatory responses were noted with any of implants 1 to 4. The results indicate that the failure of implant 1 to undergo substantial yield/elongation before failure and the lower load to failure for implant 1 relative to implants 2, 3, and 4 are not due to an absence of bone ingrowth but rather suggest that limitation of bone volume in the interface may cause implants to fail to undergo substantial yield/elongation before failure and to exhibit relatively low loads to failure.

Example 3

Prophetic Example Regarding Hip and Other Prosthesis

The hard-tissue implant, including a bulk implant, a face, pillars, and slots, as described above, may be used in hip prosthesis to allow for early ambulation or, potentially, immediate ambulation, with the avoidance of a need for grout or cement, and for intimate and immediate integration of the bone with the implant at the interface. The interface of the hard-tissue implant and the hard tissue is expected to respond to mechanical stress more like natural hard tissue than would a corresponding interface formed with a conventional implant, with potential benefits including elimination of stress shielding. The implant can be, for example, a non-metal polymer implanted at a joint articulating surface. Similarly, the hard-tissue implant may be used in shoulder prosthesis, wrist or finger joint prosthesis, ankle prosthesis, knee prosthesis, and inserts for cartilage.

Example 4

Prophetic Example Regarding Metatarsal Wedge Implants

The hard-tissue implant, including a bulk implant, a face, pillars, and slots, as described above, may be used in metatarsal wedge implants. In podiatry, there are patients for whom an implant wedge needs to be implanted in order to realign and redirect the metatarsal and tarsal elements. Conventional wedge devices tend to be inadequately fixed due to poor integration and load transfer. The hard-tissue implant as described above may allow for fixation with the potential for elimination of screws and other fixation mechanisms and may reduce the potential for implant migration and nonunion.

Example 5

Prophetic Example Regarding Screws

The hard-tissue implant, including a bulk implant, a face, pillars, and slots, as described above, may be formed as a screw including the pillars on threads or a helical face of the screw. Such a screw may be useful for spinal surgery, fixation of plates, or ligamentous repair, e.g. anterior cruciate ligament repair of the knee, with the fixation end of the screw, including the pillars, being implanted into hard tissue to allow for optimal load transfer. Such a screw may also be useful for tendon insertion and anchoring.

Example 6

Prophetic Example Regarding Dental Implants

The hard-tissue implant, including a bulk implant, a face, pillars, and slots, as described above, may also be used as a dental implant. Conventional mechanisms for fixation of dental implants having smooth surfaces or conventional surface morphologies in maxillary bone and mandibular bone are inadequate, based on poor load transfer with respect to compression and vertical shear from the bone to the dental implants and poor matching of the Young's modulus of elasticity between the dental implants and the bone. The hard-tissue implant as described above may provide improved load transfer, based on implanting of the hard-tissue implant, in the form of a dental implant, either (i) such that the pillars of the implant are oriented perpendicularly to the primary axis of compression of the maxillary or mandibular bone and penetrate the maxillary bone, or (ii) by pressing the implant into the maxillary or mandibular bone such that the pillars of the implant are oriented at an acute angle relative to the direction of the pressing and penetrate the bone. The hard-tissue implant as described above may also provide improved matching of the Young's modulus of elasticity between the implant and the hard tissue in the interface. The resulting interface may be expected to be long-lasting, resistant to stress shielding, and resilient to load.

Example 7

Prophetic Example Regarding Minimally Invasive Surgery

The hard-tissue implant, including a bulk implant, a face, pillars, and slots, as described above, may also be used in minimally invasive surgery. Current approaches for reconstructive surgery include minimally invasive surgery requiring addition or removal of only a minor or superficial portion of a hard-tissue component of a joint, finger, wrist, elbow, shoulder, knee, or (potentially) hip is required. Consequently a new interface needs to be created and inserted in the corresponding hard tissue. The hard-tissue implant as described above may be designed for early impregnation and load bearing, based on good surface integration through load bearing, with the result that no extensive use of screws or plating mechanisms would be required at the time of implantation.

Example 8

Prophetic Example Regarding Hard-Tissue Implants Made from Hard-Tissue

The hard-tissue implant, including a bulk implant, a face, pillars, and slots, as described above, may be made from a hard tissue. For example, a hard tissue such as bone, e.g. human bone, animal bone, or cadaver bone, may be machined to form the implant as described above. The implant may then be implanted in an individual, e.g. a human or animal, in need thereof, e.g. a cancer patient from whom a tumor has been removed and into which a large segment of bone may be inserted. Machining bone to form the implant may allow for more rapid ambulation, integration, and interfacial integration, in comparison to a conventional implant. Also for example, a hard tissue such as cartilage may be machined to form the implant as described above. The implant may then be implanted on another hard tissue, e.g. bone, in order to resurface the other hard tissue. Implants machined from a hard tissue may be used to replace part or all of the articulating surfaces of the hard tissues into which they are implanted, leaving most of the surrounding hard tissue in place and thus minimizing the extent of the implantation.

It will be apparent to those skilled in the art that various modifications and variations can be made without departing from the spirit and scope of the claimed invention.

What is claimed is:
1. A method of use of a hard-tissue implant in a hard tissue of an individual in need thereof, the hard-tissue implant comprising:
  (a) a bulk implant;
  (b) a face being an exterior surface of the bulk implant;
  (c) pillars for implantation into a hard tissue, the pillars being distributed on the face, across an area of at least 80 $mm^2$, and extending distally therefrom, and each pillar being integral to the bulk implant, having a distal end, having a transverse area of (200×200) to (10,000×10,000) $\mu m^2$, and having a height of 100 to 10,000 $\mu m$; and
  (d) slots to be occupied by the hard tissue, the slots being defined by the pillars and each slot having a width of 100 to 10,000 $\mu m$ as measured along the shortest distance between adjacent pillars; wherein:

the hard-tissue implant has a Young's modulus of elasticity of at least 10 GPa, has a ratio of (i) the sum of the volumes of the slots to (ii) the sum of the volumes of the pillars and the volumes of the slots of 0.40:1 to 0.90:1, does not comprise any part that is hollow, and does not comprise any non-pillar part extending to or beyond the distal ends of any of the pillars;

the method comprising:

(1) selecting the hard-tissue implant such that the ratio of (i) the product of (a) the Young's modulus of the hard-tissue implant and (b) the sum of the volumes of the pillars to (ii) the product of (a) the Young's modulus of the hard tissue and (b) the sum of the volumes of the slots is 0.80:1 to 3.8:1; and (2) implanting the hard-tissue implant in the hard-tissue of the individual.

2. The method of claim 1, wherein the implanting comprises pressing the hard-tissue implant into the hard tissue, thereby providing immediate load transfer and preventing stress shielding.

3. The method of claim 1, wherein the implanting comprises pressing the hard-tissue implant into the hard tissue, such that the pillars are oriented perpendicularly to the primary axis of tension and compression of the hard tissue and penetrate the hard tissue, thereby providing immediate load transfer and preventing stress shielding.

4. The method of claim 1, wherein the implanting comprises pressing the hard-tissue implant into the hard tissue, such that the pillars are oriented at an acute angle relative to the direction the pressing and penetrate the hard tissue, thereby providing immediate load transfer and preventing stress shielding.

5. The method of claim 1, wherein the implanting comprises pressing the hard-tissue implant into a cavity that has been milled in the hard tissue, such that the pillars penetrate the hard tissue, thereby providing immediate load transfer and preventing stress shielding.

6. The method of claim 1, wherein the hard tissue is selected from the group consisting of long bone, maxillary bone, mandibular bone, and membranous bone.

7. The method of claim 1, wherein the ratio of (i) the product of (a) the Young's modulus of the hard-tissue implant and (b) the sum of the volumes of the pillars to (ii) the product of (a) the Young's modulus of the hard tissue and (b) the sum of the volumes of the slots is 0.90:1 to 3.6:1.

8. The method of claim 1, wherein the hard-tissue implant is made of a material selected from the group consisting of implantable-grade polyetheretherketone, titanium, stainless steel, cobalt-chromium alloy, and titanium alloy.

9. The method of claim 1, wherein the hard-tissue implant is made of another hard tissue selected from the group consisting of an autologous hard tissue, an allogeneic hard tissue, a xenogeneic hard tissue, human cartilage, animal cartilage, a human bone, an animal bone, and a cadaver bone.

10. The method of claim 1, wherein the hard-tissue implant is made of implantable-grade polyetheretherketone, the transverse area of each pillar is (350×350) to (450×450) $\mu m^2$, the height of each pillar is 400 to 600 μm, the width of each slot is 190 to 210 μm, and the ratio of (i) the sum of the volumes of the slots to (ii) the sum of the volumes of the pillars and the volumes of the slots is 0.51:1 to 0.60:1.

11. The method of claim 1, wherein the hard-tissue implant is made of titanium, the transverse area of each pillar is (350×350) to (450×450) $\mu m^2$, the height of each pillar is 400 to 600 μm, the width of each slot is 390 to 410 μm, and the ratio of (i) the sum of the volumes of the slots to (ii) the sum of the volumes of the pillars and the volumes of the slots is 0.70:1 to 0.76:1.

\* \* \* \* \*

UNITED STATES PATENT AND TRADEMARK OFFICE
CERTIFICATE OF CORRECTION

PATENT NO.         : 9,333,081 B2
APPLICATION NO.    : 14/288796
DATED              : May 10, 2016
INVENTOR(S)        : Picha et al.

Page 1 of 1

It is certified that error appears in the above-identified patent and that said Letters Patent is hereby corrected as shown below:

In the specification:

Column 21, line 11: please delete "321" and replace it with --3.21--

Column 21, line 13: please delete "321" and replace it with --3.21--

Signed and Sealed this
Twenty-sixth Day of July, 2016

Michelle K. Lee
*Director of the United States Patent and Trademark Office*